(12) United States Patent
Tannhauser

(10) Patent No.: US 7,083,637 B1
(45) Date of Patent: Aug. 1, 2006

(54) METHOD AND APPARATUS FOR ADJUSTING FLEXIBLE AREAL POLYMER IMPLANTS

(76) Inventor: Robert J. Tannhauser, 265 Holland Ct., Bridgewater, NJ (US) 08807

( * ) Notice: Subject to any disclaimer, the term of this patent is extended or adjusted under 35 U.S.C. 154(b) by 652 days.

(21) Appl. No.: 09/589,242

(22) Filed: Jun. 7, 2000

Related U.S. Application Data
(60) Provisional application No. 60/138,231, filed on Jun. 9, 1999.

(51) Int. Cl.
*A61B 17/04* (2006.01)

(52) U.S. Cl. .................................................... 606/228
(58) Field of Classification Search ................ 604/509, 604/148; 606/148, 119, 185, 228, 222
See application file for complete search history.

(56) References Cited

U.S. PATENT DOCUMENTS

| | | | |
|---|---|---|---|
| 3,182,662 A | 5/1965 | Shirodkar | |
| 3,212,502 A | 10/1965 | Myers | |
| 3,311,110 A | 3/1967 | Shingerman | |
| 3,372,695 A | 3/1968 | Beliveau et al. | |
| 3,472,232 A | 10/1969 | Earl | |
| 3,608,095 A | 9/1971 | Barry | |
| 3,763,860 A | 10/1973 | Clarke | |
| 3,858,783 A | 1/1975 | Kapitanov et al. | |
| 3,924,633 A | 12/1975 | Cook et al. | |
| 4,037,603 A | 7/1977 | Wendorff | |
| 4,128,100 A | 12/1978 | Wendorff | |
| 4,235,238 A | 11/1980 | Ogiu et al. | |
| 4,392,495 A | 7/1983 | Bayers | |
| 4,441,497 A | 4/1984 | Paudler | |
| 4,509,516 A | 4/1985 | Richmond | |
| 4,549,545 A | * 10/1985 | Levy | 606/228 |
| 4,946,467 A | 8/1990 | Ohi et al. | |

(Continued)

FOREIGN PATENT DOCUMENTS

| | | |
|---|---|---|
| AU | B278089 | 6/1967 |
| AU | B441561 | 1/1973 |
| DE | 3223153 C1 | 8/1983 |
| DE | 42 20 283 A1 | 12/1993 |
| DE | 4334419 | 4/1995 |
| EP | 0598976 | 6/1994 |
| EP | 0 668 056 A1 | 8/1995 |
| EP | 0 774 240 A1 | 5/1997 |
| EP | 0941712 | 9/1999 |
| EP | 0 941 712 A1 | 9/1999 |
| EP | 1 025 811 AW | 8/2000 |
| EP | 1025811 | 8/2000 |
| SE | 503271 | 4/1996 |
| WO | WO 9003766 | 4/1990 |
| WO | WO 9606567 | 3/1996 |
| WO | WO 96/06597 | 3/1996 |
| WO | WO 97/13465 | 4/1997 |
| WO | WO 9831301 | 7/1998 |
| WO | WO 98/31301 | 7/1998 |
| WO | WO 01/06951 A1 | 2/2001 |
| WO | WO 02/28312 A1 | 4/2002 |
| WO | WO 02/38079 | 5/2002 |
| WO | WO 2004/012626 A1 | 2/2004 |

OTHER PUBLICATIONS

Supplementary Partial European Search Report dated Sep. 23, 2004, for corresponding EP application 00928947.1.

(Continued)

*Primary Examiner*—Vy Bui

(57) ABSTRACT

A minimally invasive approach to adjusting the amount of support on an anatomical structure. The methods and apparatus described include the use of a tape for supporting an anatomical structure. Adjustment may be achieved by use of bulking agents applied either directly to the site or into a containment device Lo located within proximity of the tape and such that it works in conjunction with the tape to support the anatomic structure. An alternative approach utilizes mechanical means for adjusting the effective length of the supporting arms of the tape used to support the anatomical structure.

14 Claims, 27 Drawing Sheets

U.S. PATENT DOCUMENTS

| | | | |
|---|---|---|---|
| 5,013,292 A | | 5/1991 | Lemay |
| 5,032,508 A | | 7/1991 | Naughton et al. |
| 5,080,667 A | * | 1/1992 | Chen et al. ............... 606/225 |
| 5,112,344 A | * | 5/1992 | Petros ............... 128/DIG. 25 |
| 5,180,385 A | | 1/1993 | Sontag |
| 5,250,033 A | | 10/1993 | Evans et al. |
| 5,281,237 A | | 1/1994 | Gimpelson |
| 5,337,736 A | | 8/1994 | Reddy |
| 5,362,294 A | * | 11/1994 | Seitzinger ............... 600/37 |
| 5,368,595 A | | 11/1994 | Lewis |
| 5,368,756 A | | 11/1994 | Vogel et al. |
| 5,382,257 A | | 1/1995 | Lewis et al. |
| 5,383,904 A | * | 1/1995 | Totakura et al. ............ 606/228 |
| 5,403,328 A | | 4/1995 | Shallman |
| 5,441,508 A | | 8/1995 | Gazielly et al. |
| 5,450,860 A | | 9/1995 | O'Connor |
| 5,507,796 A | | 4/1996 | Hasson |
| 5,582,188 A | * | 12/1996 | Benderev et al. ............ 128/898 |
| 5,611,515 A | * | 3/1997 | Benderev et al. ............ 128/898 |
| 5,628,756 A | | 5/1997 | Barker, Jr. et al. |
| 5,645,568 A | * | 7/1997 | Chervitz et al. ............ 606/228 |
| 5,741,299 A | * | 4/1998 | Rudt ............... 606/224 |
| 5,816,258 A | | 10/1998 | Jervis |
| 5,836,315 A | * | 11/1998 | Benderev et al. ............ 128/898 |
| 5,840,011 A | | 11/1998 | Landgrebe et al. |
| 5,855,549 A | | 1/1999 | Newman |
| 5,860,425 A | | 1/1999 | Benderev et al. |
| 5,899,909 A | | 5/1999 | Claren et al. |
| 5,899,999 A | * | 5/1999 | De Bonet ............... 707/104.1 |
| 5,934,283 A | | 8/1999 | Willem et al. |
| 5,935,122 A | | 8/1999 | Fourkas et al. |
| 5,945,122 A | | 8/1999 | Abra et al. |
| 5,997,554 A | | 12/1999 | Thompson |
| 6,010,447 A | | 1/2000 | Kardjian |
| 6,030,393 A | | 2/2000 | Corlew |
| 6,042,534 A | * | 3/2000 | Gellman et al. ............... 600/30 |
| 6,050,937 A | | 4/2000 | Benderev |
| 6,110,101 A | * | 8/2000 | Tihon et al. ............... 600/37 |
| 6,117,067 A | * | 9/2000 | Gil-Vernet ............... 600/30 |
| 6,221,005 B1 | | 4/2001 | Bruckner et al. |
| 6,273,852 B1 | | 8/2001 | Lehe |
| 6,306,079 B1 | | 10/2001 | Trabucco |
| 6,334,446 B1 | | 1/2002 | Beyar |
| 6,382,214 B1 | | 5/2002 | Raz et al. |
| 6,406,423 B1 | | 6/2002 | Scetbon |
| 6,475,139 B1 | | 11/2002 | Miller |
| 6,491,703 B1 | | 12/2002 | Ulmsten |
| 6,605,097 B1 | | 8/2003 | Lehe et al. |
| 6,612,977 B1 | | 9/2003 | Staskin et al. |
| 6,691,711 B1 | | 2/2004 | Raz et al. |
| 2001/0018549 A1 | | 8/2001 | Scetbon |
| 2001/0049457 A1 | | 12/2001 | Lehe et al. |
| 2001/0049467 A1 | | 12/2001 | Lehe |
| 2002/0028980 A1 | | 3/2002 | Thierfelder et al. |
| 2002/0058959 A1 | | 5/2002 | Gellman |
| 2002/0077526 A1 | | 6/2002 | Kammerer et al. |
| 2002/0091373 A1 | | 7/2002 | Berger |
| 2002/0188169 A1 | | 12/2002 | Kammerer et al. |
| 2003/0004395 A1 | | 1/2003 | Therin |
| 2003/0023138 A1 | | 1/2003 | Luscombe |
| 2003/0149440 A1 | | 8/2003 | Kammerer et al. |
| 2003/0176762 A1 | | 9/2003 | Kammerer |
| 2003/0195386 A1 | | 10/2003 | Thierfelder et al. |
| 2003/0220538 A1 | | 11/2003 | Jacquetin |
| 2004/0039453 A1 | | 2/2004 | Anderson et al. |

OTHER PUBLICATIONS

Giberti, "Transvaginal Sacrospinous Colpopexy by Palpation–A New Minimally Invasive Procedure Using an Anchoring System", UROLOGY vol. 57 (2001) pp 666–669.

Cosson et al, "Cystocele Repair by Vaginal Patch", Progres en Urologie vol. 11 (2001) pp. 340–346.

Collinet et al, "The Vaginal Patch for Vaginal Cure of Cystocele", J. Gynecol. Obstet. Biol. Reprod. vol. 29, No. 2 (2000) pp 197–201.

Leanza et al, "New Technique for Correcting Both Incontinence and Cystocele: T.I.C.T.", Urogynaecologia International Journal vol. 15, No. 3 (2001) pp 133–140.

EPO Supplementary Search Report dated Aug. 2, 2004, for corresponding EP application 02776559.3.

"TVT Tension–free Vaginal tape, Minimally Invasive Highly Effective Treatment for Female Stress Urinary Incontinence", Gynecare, Ethicon, Inc., 1999, pp. 1–6.

"AMS Spare Sling System", American Medical Systems, Inc., Minnetonka, MN, 2001, pp. 1–6.

Petros, P.E. Papa, "Vault Prolapse II: Restoration of Dynamic Vaginal Supports by Infracoccygeal Sacropexy, an Axial Day–Case Vaginal Procedure", International Urogynecol Journal (2001) vol. 12, pp. 296–303, Springer–Verlag London Ltd.

Petros, P.E. Papa, Vault Prolapse I: "Dynamic Supports of the Vagina", International Urogynecol Journal (2001) vol. 12, pp. 292–295, Springer–Verlag London Ltd.

PCT International Search Report PCT/US02/14770 dated Oct. 29, 2002 (related case GYN–90–PCT).

Cosson et al, "Cyslocele Repair by Vaginal Patch", Progres en Urologie vol. 11 (2001) pp. 340–346.

Co–pending appln. "Surgical Instrument and Method for treating Female Urinary Incontinence", U.S. Appl. No. 09/718,546, filed Nov. 20, 2000, Inventor: Ulf Ulmsted, et al.).

Co–pending appln. "Surgical Instrument and Method for Treating Female Urinary Incontinence", U.S. Appl. No. 60/356,697, filed Feb. 14, 2002, Inventor Gene W. Kammerer.

* cited by examiner

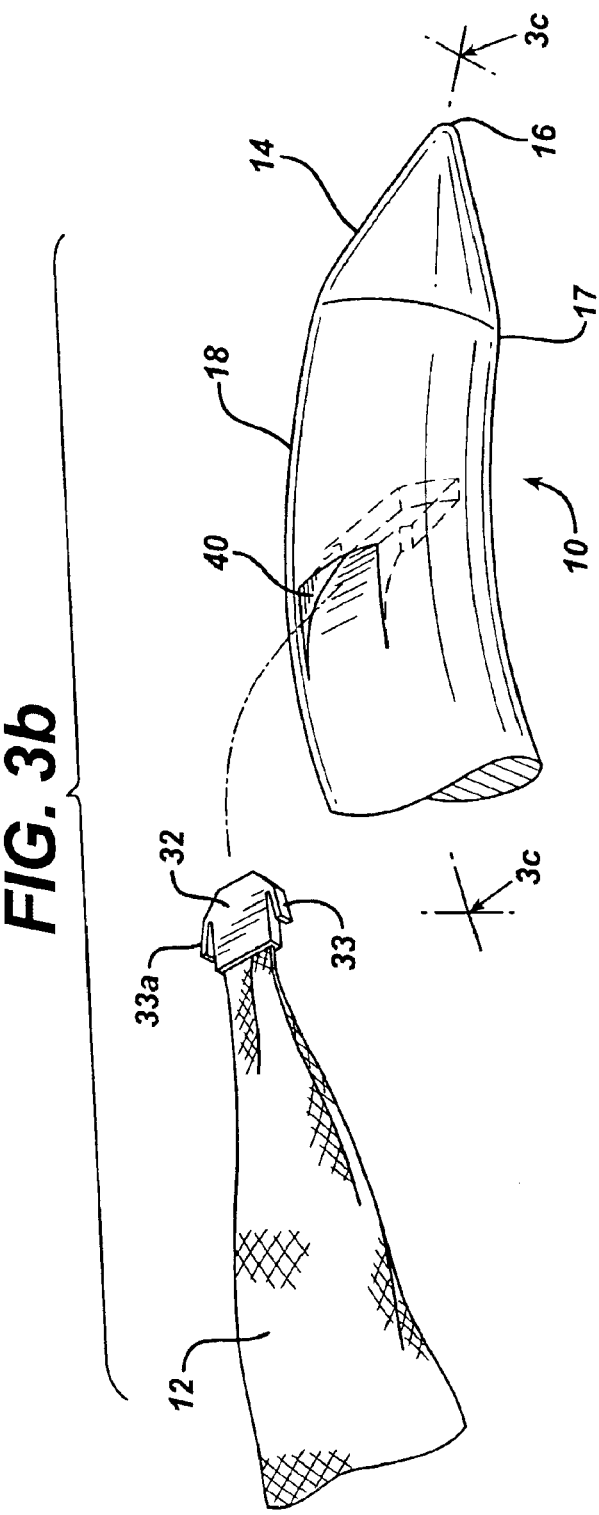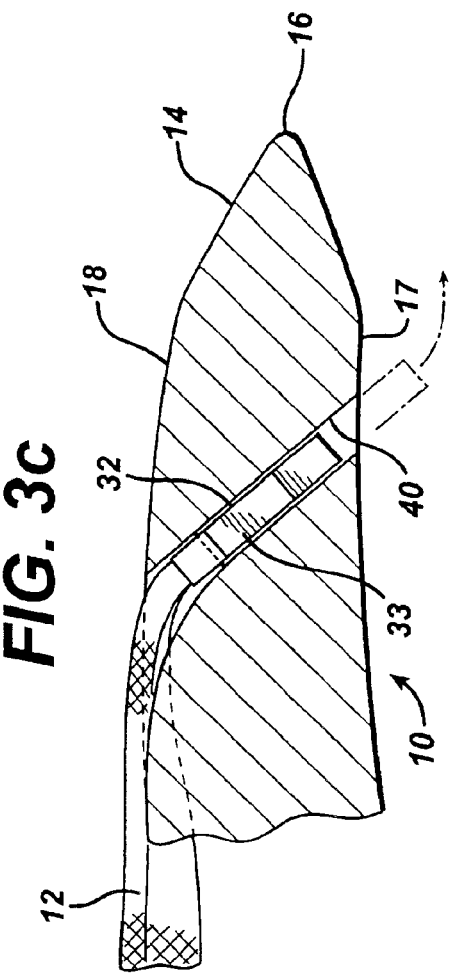
FIG. 3b
FIG. 3c

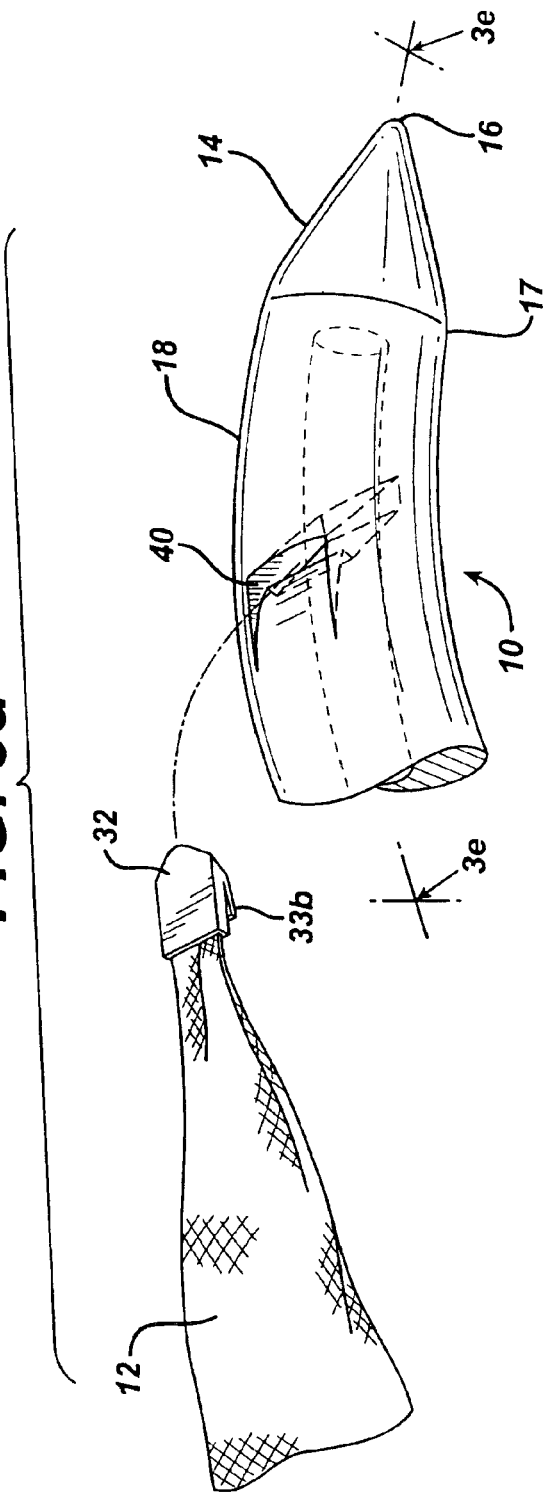
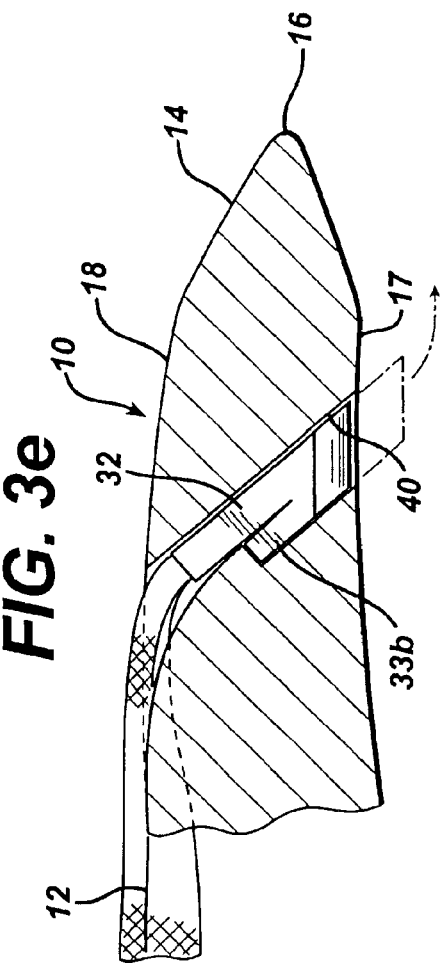

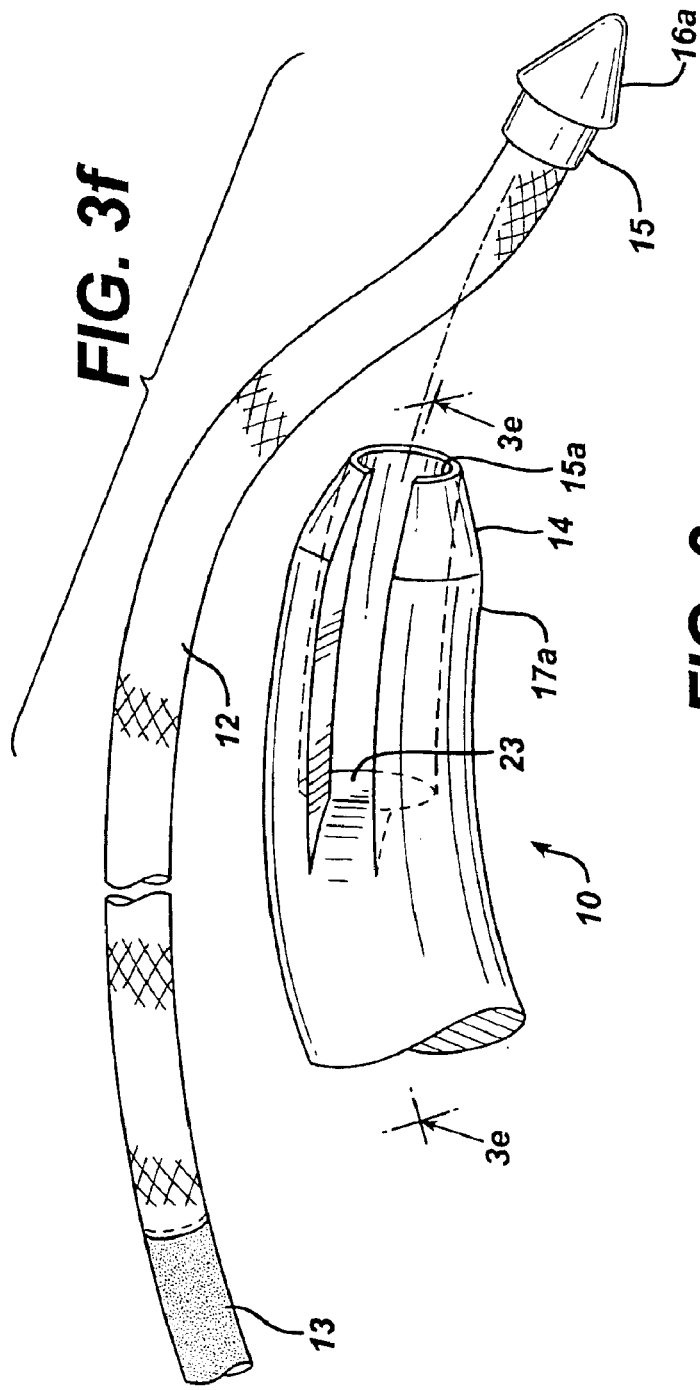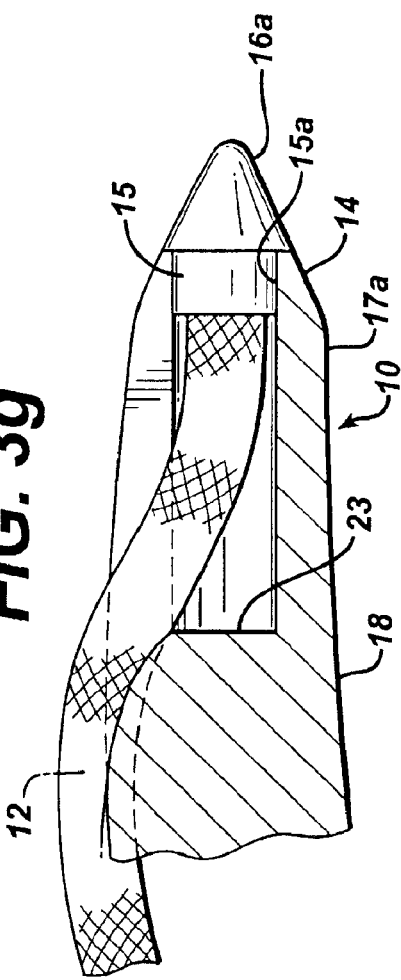

METHOD AND APPARATUS FOR ADJUSTING FLEXIBLE AREAL POLYMER IMPLANTS

CROSS REFERENCE TO RELATED APPLICATION

The present invention claims the benefit of earlier-filed U.S. provisional patent application, Ser. No. 60/138,231, filed on Jun. 9, 1999, which is hereby incorporated by reference in its entirety herein.

BACKGROUND OF THE INVENTION

The present invention relates generally to a minimally invasive approach to adjust a flexible a real polymer implant for supporting an anatomical structure and further relates to an approach especially useful for use with implants that support the urethra for treating female urinary incontinence.

Women account for more than 11 million of incontinence cases. Moreover, a majority of women with incontinence suffer from stress urinary incontinence (SUI). Women with SUI involuntarily lose urine during normal daily activities and movements, such as laughing, coughing, sneezing and regular exercise.

SUI may be caused by a functional defect of the tissue or ligaments connecting the vaginal wall with the pelvic muscles and pubic bone. Common causes include repetitive straining of the pelvic muscles, childbirth, loss of pelvic muscle tone, and estrogen loss. Such a defect results in an improperly functioning urethra. Unlike other types of incontinence, SUI is not a problem of the bladder.

Normally, the urethra, when properly supported by strong pelvic floor muscles and healthy connective tissue, maintains a tight seal to prevent involuntary loss of urine. When a woman suffers from the most common form of SUI, however, weakened muscle and pelvic tissues are unable to adequately support the urethra in its correct position. As a result, during normal movements when pressure is exerted on the bladder from the diaphragm, the urethra cannot retain its seal, permitting urine to escape. Because SUI is both embarrassing and unpredictable, many women with SUI avoid an active lifestyle, shying away from social situations.

U.S. Pat. No. 5,112,344 describes a method and apparatus for treating female incontinence. The surgical instrument for the application of a filamentary element into the body comprises a tubular shaft having a handle at one end and a flexible needle slidably receivable in the shaft and adapted at one end to receive a filamentary element. The method of treating female incontinence comprises looping a filamentary element between the wall of the vagina and the rectus abdominis sheath in the anterior wall of the abdomen whereby it passes to each side of the urethra, adjusting the loop to bring the vaginal wall and the urethra into the correct spatial relationship to the pubis allowing the development of scar tissue between the vaginal wall and the anterior wall of the abdomen pubic symphysis and removing the filamentary element.

U.S. Pat. No. 5,899,909 discloses a surgical instrument comprising a shank having a handle at one end and connecting means at the other end to receive, one at a time, two curved needle-like elements which are connected at one end to one end of a tape intended to be implanted into the body. In practice, the tape is passed into the body via the vagina first at one end and then at the other end at one side and the other, respectively, of the urethra to form a loop around the urethra, located between the urethra and vaginal wall. The tape is extended over the pubis and through the abdominal wall and is tightened. The tape ends are cut at the abdominal wall, and the tape is left implanted in the body. U.S. Pat. No. 5,899,909 is incorporated herein by reference.

While implanting a tape, it is often difficult to determine the most suitable amount of support to provide to the urethral structure. An optimal amount of support is defined as that which provides relief from incontinence and simultaneously provides for normal micturition. Even if the most optimal amount of support is provided during implantation, it is possible that the surrounding tissues will change during the healing process or simply due to aging. As a result, the optimal amount of support is subject to change.

European Patent 0941 712 A1, Jose Gil-Vemet Vila, describes an approach to adjusting urethral support by use of an expandable container implanted remotely from the urethra and connected to a mesh supporting the urethra. While this provides adjustment capabilities, the associated surgical procedure is invasive and complex. The container is also complex and requires features to assure that the suspending threads are not a braided. The container is preferably located in adipose tissue in the abdominal region. The container's location exposes it to distortion whenever there are external forces applied to the abdominal area. This in turn is expected to transiently change the degree of support to the urethra whereas it is desirable to provide a fairly constant level of support. Since the mesh support is directly in contact with the urethra, the fluctuations of support to the urethra can become irritating to the surrounding tissue.

U.S. Pat. No. 6,042,534, Gellman et al., describes the use of a visual indicator that may be radiopaque. However, there is no specific description of how to achieve this effect and makes no mention of its use with a tape support device. Further, the purpose of this indicator is solely for assessment of the relative position of the sling used to support the urethra. Gellman is silent with respect to the need to adjust the sling after it is in place.

U.S. Pat. No. 5,611,515, Theodore V. Benderev et al., describes the use of a suture tensioning devices in conjunction with bladder neck suspension. These tensioners are used to adjust the tension on sutures used to hold a supportive sling in place on the bladder neck. Prior to tying, sutures are appropriately tensioned by advancing the suture around a suture tensioner and tying in a conventional manner. Thereafter, the suture tensioner is removed and the surgical site prepared and closed in a conventional manner. While this technique is fine for establishing the initial tension to the sling, it does not allow for post implantation adjustment. Also, this approach is fine where the sling is suspended with sutures or other filament means. However, such tensioning devices are unsuitable for tapes implanted such as those associated with the GYNECARE TVT Tension-Free Support for Incontinence.

International Patent WO 98/31301 discloses an implantable continence device that consists of a hydraulic and mechanical component.

Therefore there is a need to be able to adjust the level of support to the urethra in a less complicated manner and with no urethra-mesh contact. Further, the adjustment should be located in close proximity to where the support is needed.

The present invention discloses devices and methods for adjusting the support of internal anatomical organs both during and after implantation. In particular, the invention is intended to be especially useful for use with implants that support the urethra.

SUMMARY OF THE INVENTION

The invention overcomes the deficiencies of the prior art and provides for an improved apparatus and method for adjusting the level of support provided to an anatomical structure by an implanted tape. The invention finds particular benefit to the treatment of female urinary incontinence.

In particular the invention is useful with system for the treatment of female stress urinary incontinence. The system provides a surgical instrument comprising a handle at one end and connecting means at the other end to receive, one at a time, two curved needle-like elements, each of which has a modified tip. The needle may have a constant or varying diameter. Each needle connects at one end to separate ends of a tape intended to be implanted within the body. In practice, a first end of the tape is passed, via one of the curved needles, into the body via the vagina at one side of the urethra. The needle and first end of the tape pass over the pubis and through the abdominal wall. The second needle element connects to the second end of the tape and passes into the body via the vagina at the opposite site of the urethra from the first end of the tape thereby forming a loop or sling around the urethra with the tape. The second end of the tape is extended over the pubis and through the abdominal wall. The tape ends are cut at the abdominal wall, and the tape is left in the body.

The invention further provides for a single curved needle element having a modified tip. The needle may have a constant or varying diameter and further provides for a easy attachment means enabling the surgeon to connect both the first and second tape ends to the single needle to perform the above-stated procedure.

In both embodiments, the invention provides for devices and methods for adjusting the level of support provided to the urethra by an implanted tape. Two approaches are offered. One relates to the use of bulking agents, both contained and directly injected into surrounding tissues. In this approach, detectable markers are provided to guide the clinician during the injection process. The second approach offers mechanical means of adjusting the effective length of supporting arms of a tape used to support the urethra. These devices include threadedly adjustable constructions.

The object of the invention is to provide a method for adjusting the level of support to an anatomical structure offered by an implanted tape.

An advantage of the invention is that it provides for continual adjustment capabilities to an implanted tape for supporting an anatomical structure.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

FIGS. 3a–g embodiments of means for attaching the tape to the needle;

DETAILED DESCRIPTION OF THE INVENTION

Before explaining the present invention in detail, it should be noted that the invention is not limited in its application for the treatment of female incontinence or use to the details of construction and arrangement of parts illustrated in the accompanying drawings and description, because the illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

The invention discloses an apparatus and method for treating SUI. A tape is passed through pelvic tissue and positioned underneath the urethra, creating a supportive sling. The tape provides a structure means for tissue in growth and thereby provides a newly created body tissue supporting means for the urethra. When pressure is exerted upon the lower abdomen, such as during a cough or sneeze the tape provides support to the urethra, allowing it to keep its seal and prevent the unwanted discharge of urine.

Figure 1:
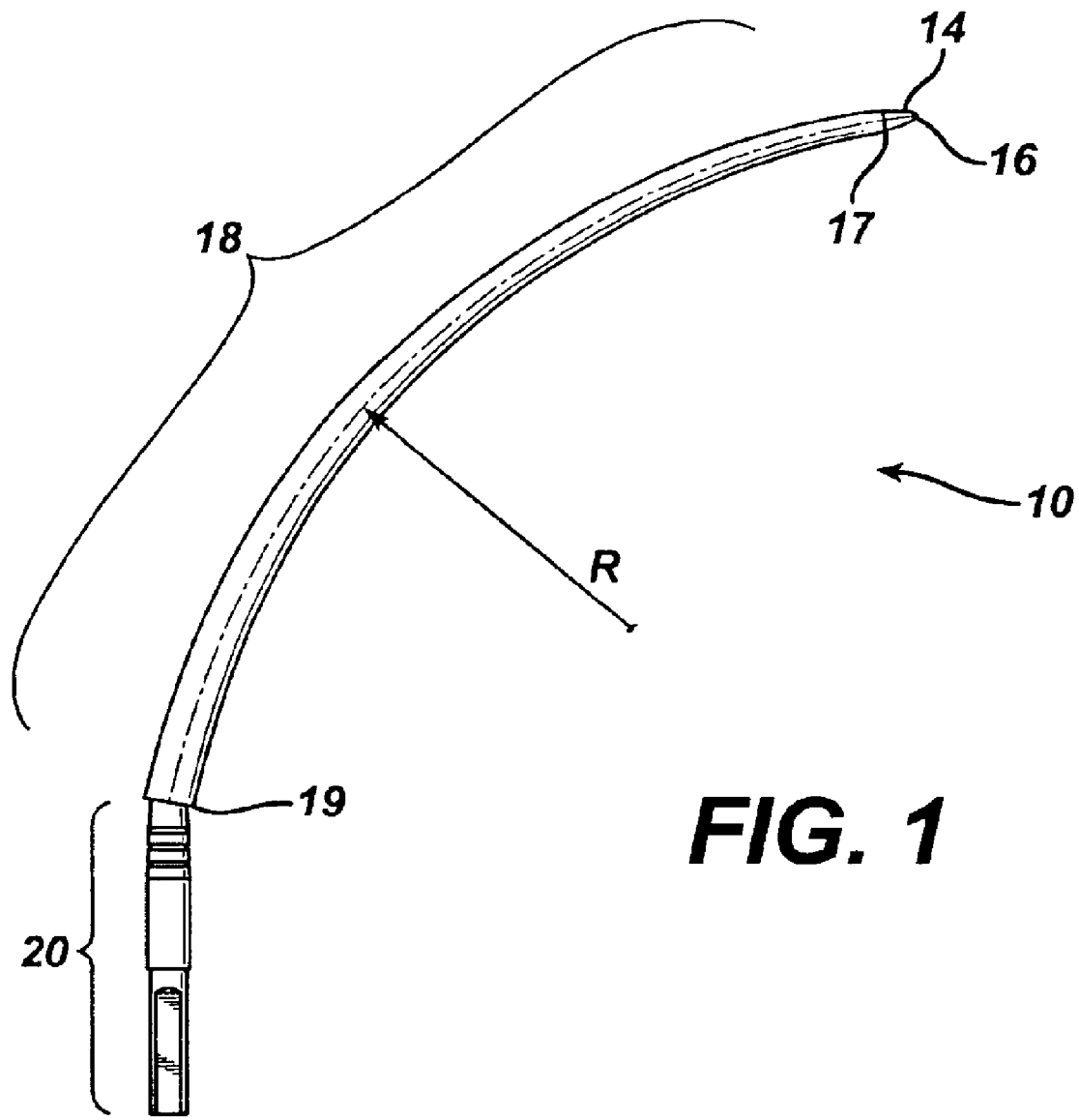
FIG. 1 is a view of the needle for use with the tape mesh.
Figure 2A:
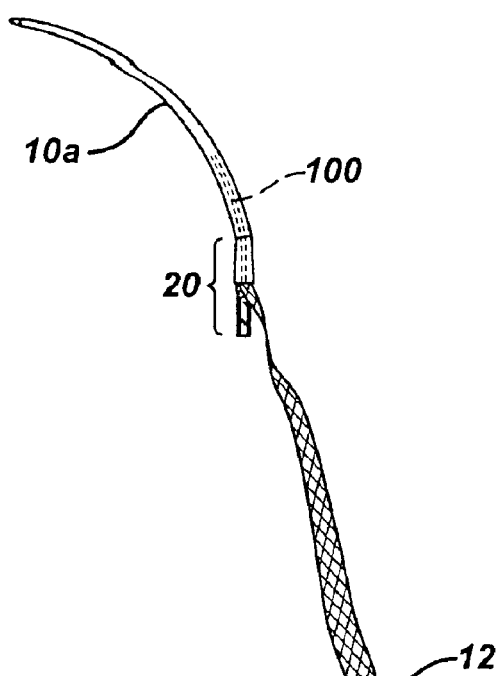
FIG. 2a is a side view of two needles and a tape interconnecting the needles.
Figure 2A:
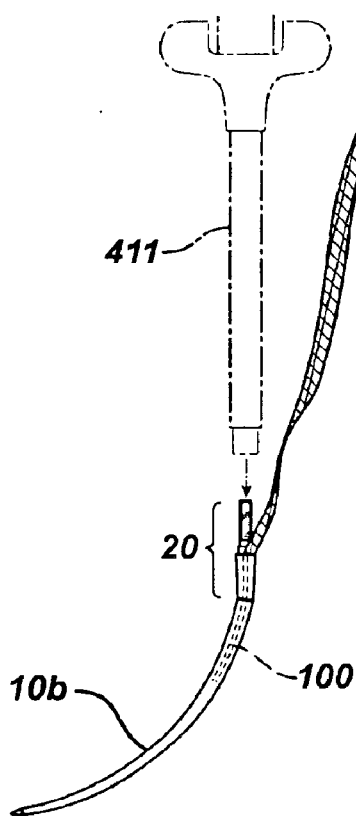

Referring to FIGS. 1 and 2a, the surgical instrument comprises a needle-like element 10 that attaches to a mesh tape 12. Needle element 10 defines a certain radius R to perform the surgical procedure discussed herein. The distal end of needle element 10 terminates at a conical section 14 having a tip 16. Alternate configurations, such as a blade-like, arrow or burrtips are also possible. Preferably, tip 16 is blunt, wherein the tip 16 has a radius of about 0.6 millimeters. A blunt tip is preferred since it is less likely to stick in bone or penetrate bladder wall tissue or blood vessel wall tissue as will be appreciated from the method of implanting the tape as described below.

The proximal end of needle 10 terminates in an attachment segment 20 that is adapted to mate and lock into a handle 411 as disclosed in U.S. Pat. No. 5,899,909, previously incorporated herein by reference.

Disposed between cone portion 14 and segment 20 is a curved shaft segment 18 having a distal end 17 and a proximal end 19. The shape of shaft 18 extends substantially a quarter of a circle in order to follow substantially the profile of the pubis between the vagina and the abdominal wall. For the purposes of the method as will be discussed in more detail below, shaft 18 has a preferred radius R of about 106 millimeters. The diameter of the curved shaft segment 18 may be constant or the diameter of segment 18 transitions from a smaller diameter at distal end 17 to a larger diameter at proximal end 19. The minimum diameter of distal end 17 may be as small as 0.5 mm due to the minimal stresses at this point. The minimal diameter of proximal end 19 is about 4 mm. Preferably, the diameter at the proximal end is about 6 mm, and reduces in a continuous manner to a diameter of about 3 mm at the distal end 17. This design takes into account, that in the method to implant the tape 12, the bending stresses are lowest at distal end 17, while the bending stresses are highest at the proximal end 19. Stated differently, during the procedure, the inner bending moment at distal end 17 is negligible, while the inner bending moment at the proximal end 19 is substantial.

Needle 10 is preferably has a circular cross section and is made from a material that is compatible with the human body. It is also preferred that needle 10 is made from a material that can be autoclaved to enable multiple surgical procedures of needle 10. Preferably, needle 10 is made from 303 stainless steel. The surface of shaft 18 may be smooth, preferably polished, to facilitate penetration of the soft tissue. Alternatively, the surface of needle 10 may have a somewhat rougher surface. A rougher surface would result in slightly additional tissue trauma, which in turn stimulates fibroblast activity around the tape 12.

Needle 10 may be manufactured as a single, continuous unit, or alternatively, curved portion 18 may be manufactured separately from linear portion 20. In this manner the two pieces would attach using any conventional attaching means, such as, screwing, or other conventional means as is known to those skilled in the art.

Figure 2B:
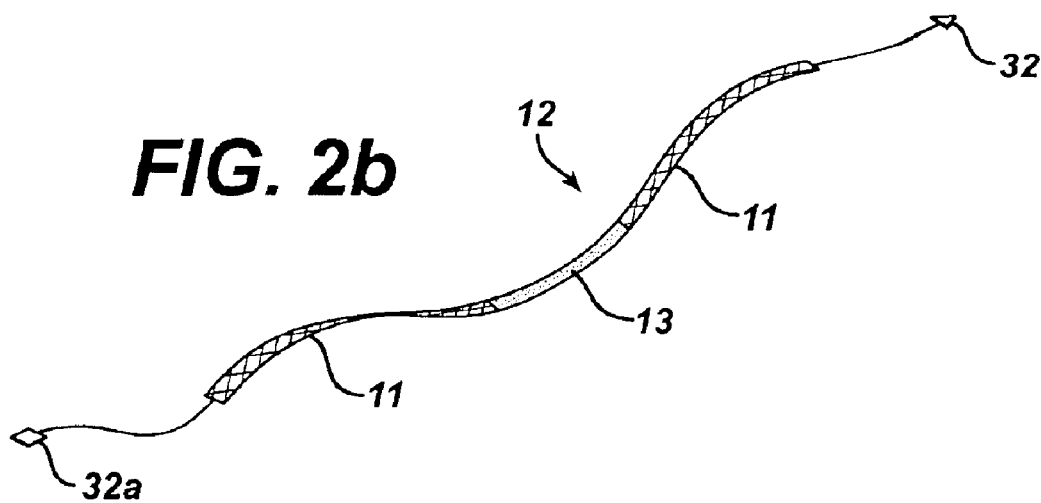
FIGS. 2b–d are alternate embodiments of the tape and connecting means between the tape and needle.
Figure 2C:
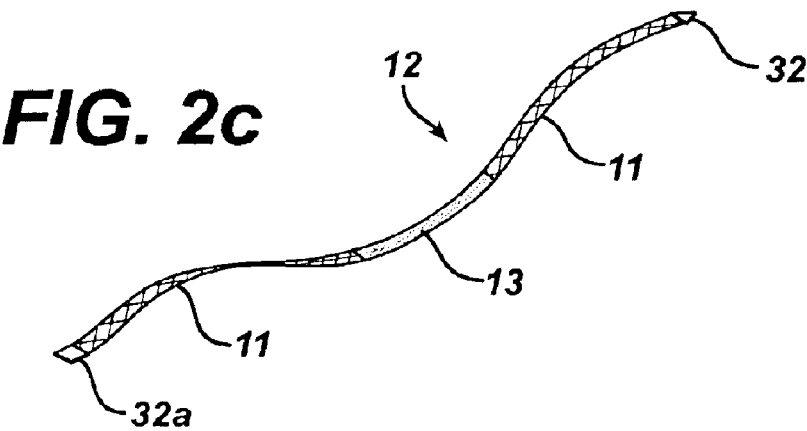

Referring to FIGS. 2a–d, tape 12 comprises any tissue-compatible synthetic material, or any natural material, including, but not limited to, autologous, allograft, xenograft, a tissue engineered matrix, or a combination thereof. An exemplary synthetic material is PROLENE® polypropylene mesh, a mesh having a thickness of 0.7 mm and openings of about 1 mm manufactured by Ethicon, Inc., Somerville, N.J., U.S.A. This material is approved by the U.S. Food and Drug Administration for implantation into the human body. A still further embodiment of the tape 12 is a combination of a synthetic material 11 and a natural material 13 centered between the synthetic material 11 as shown in FIGS. 2b–c. A still further embodiment of the tape 12 includes a combination of synthetic material 11 and natural material 13, whereby the natural material is placed over or incorporated within a generally central portion of the synthetic material 11. One advantage of the tape configurations is that natural material 13 is along the center region of tape 12 so that after installation of tape 12, natural material 13 is positioned below the urethra and eliminates possible erosion issues at the interface of the urethra and tape. Natural material 13 may be connected to the synthetic material 11 by means of sewing, a bio-compatible glue, cell culturing techniques or other known means.

Tape 12 may be of any convenient shape that suits the intended purpose of the invention. An exemplary width is about 1 cm and the length would be dependent upon the size of the female undergoing the procedure. Tape 12 may be single or double ply, generally planar in structure, or tubular (FIG. 2d) to provide additional supporting strength and more surface area on which tissue fibers may attach.

Moreover, tape 12 may consist of different types of material, such as a bioabsorbable and non-bioabsorbable material. Tape 12 may also be coated with an antimicrobial additive to prevent or minimize infection and a lubricous coating, for example, a bioabsorbable hydrogel, to facilitate the tape passing through the tissue as discussed below. Preferably, tape 12 is covered by a removal plastic sheath as disclosed in U.S. Pat. No. 5,899,909. The tape may also be made radio-opaque and/or of a contrasting color to the body tissue to allow for future diagnostic visualization.

Referring to FIGS. 4a–f, tape 12 is further modified to include an expandable container or chamber 100 positioned on the tape 12 so the chamber 100 is located between the urethra and tape surface after the surgical procedure, discussed below. The container 100 serves to limit migration and/or resorption of the bulking agent. Further, the chamber 100 expands or contracts by either injecting into or extracting bulking material from the chamber 100.

The container 100 may be made of a biocompatable material such as a hydrogel (i.e., crosslinked methacrylic-PEG esters, PHEMA, PMMA, phospholipid-like methacrylic polymers, radiation crosslinked PEO or PEG), polypropylene, polyester, silicone, or polyurethane. The container may be an integral part of the tape or may be slidably attached so that its position is such that it will work in unison with the tape in supporting the urethra. This should be near the center of the mesh so that after implantation, container 100 is positioned below the urethral area. Optionally, container 100 has a touchable internal valve element 101 to permit the surgeon to palpatate the area prior to injecting or removing the bulking agent. Alternatively, the bulking agent may be injected and removed via a two-way eternal port 102. When a bulking agent is injected into container 100 the tissue between mesh and urethra will expand. This results in two effects; a simple vertical lifting due to expansion and a vertical lifting due to stretching the outside of the mesh. A suitable bulking agent may be water or saline.

Preferably, container 100 has no voids when empty and has a height of about 0.5 cm to about 2 cm and a length from about 2 cm to about 4 cm. Container 100 may be an cube-like expandable element of FIG. 4a, or a dome-shape of FIG. 4b.

Figure 4A:
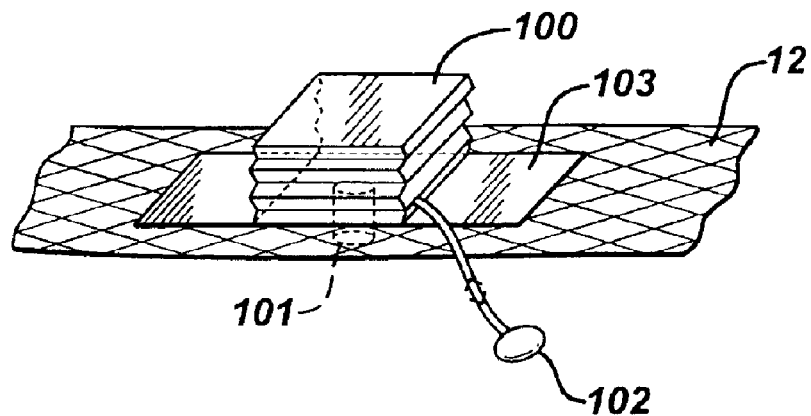
FIGS. 4a–f are alternate embodiments providing an expandable container associated with the tape mesh.
Figure 4B:
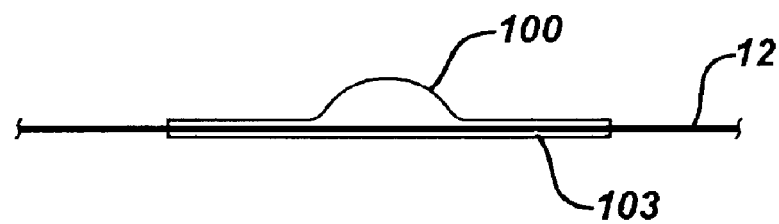
Figure 4C:
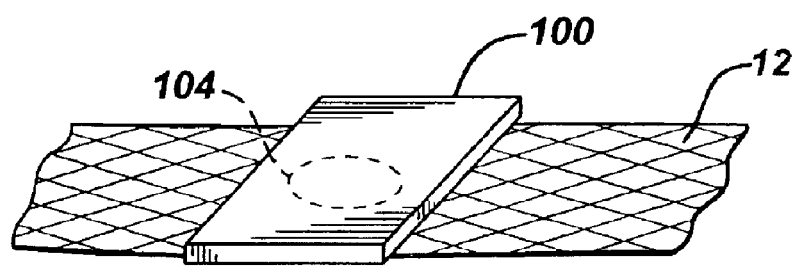
Figure 4D:
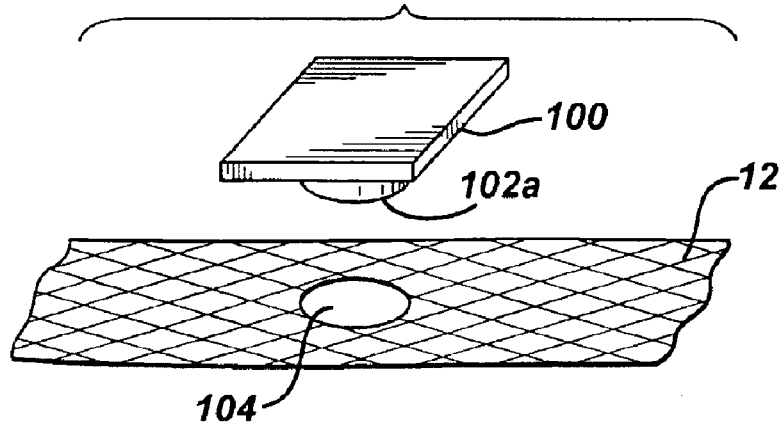

The container 100 also includes a foot portion 103 suitable for attachment to tape 12. Attachment may be achieved by incorporating the tape into the foot with the hydrogel being on both sides of the tape as shown in FIG. 4b. Foot portion 103 is preferred when the tape is a polypropylene mesh since polypropylene materials do not accept adhesive material. This configuration is preferred because container 100 increases the effective bending stiffness of the tape 12 in the area of the container's attachment.

Alternatively, container 100 may comprise two chambers 100a, 100b in fluid communication with each other. Alternatively, the two chambers 100a, 100b may be separate and effectively two containers. However, they may be linked together by a common injection port. This configurations allows for tissue expansion both underneath and lateral to the urethra.

The addition of container 100 to the mesh 12 acts to increase the effective bending stiffness of the mesh 12 in the area of the attachment of container 100. The increased bending stiffness provides additional support to the urethra when the mesh 12 is implanted. The bending stiffness further increases when the container 100 is filled with bulking agents If container 100 is semi-permeable, the injected bulking agent can be designed to take advantage of osmotic tension to assure adequate fill volume. Similarly, a container 100 fabricated with a hydrogel may have a slight osmotic tension adjustment effect. Further, drug delivery can be achieved by diffusion of the injected material from within the container to the surrounding tissues.

EXAMPLE 1

A container 100 was manufactured utilizing a commercially available 6 cm×4 cm tissue expanding device available from Mentor Deutschland GmbH, catalog number 350–5301 M. The tissue-expanding device includes a remote two-way injection port 102 attached to one end. The tissue-expanding device was cut in the longitudinal direction to a width of 2 cm. The upper and lower walls were temporarily sealed together along the cut lengths using cyanoacrylate glue and later permanently sealed using the silicon adhesive, below. This results in a container having a width of approximately 1.5 cm. A polypropylene mesh was placed on the container. A silicon adhesive (silicon monomer and a catalyst component) was brushed onto the mesh segment overlying the container and the underlying container and. After curing over night, the mesh was firmly attached to the container. The expandable container with external port was easily and reversible expandable. The manufactured container 100 provided the added bending stiffness along the area of its attachment to the mesh.

EXAMPLE 2

A configuration similar to Example 1 except that the injection port is incorporated as an integral part of one side of the expandable container. Container mounts to the mesh 12 by providing an opening 104 in the mesh 12 for the introduction of the injection port 102a as shown FIGS. 4c–d.

Figure 4E:
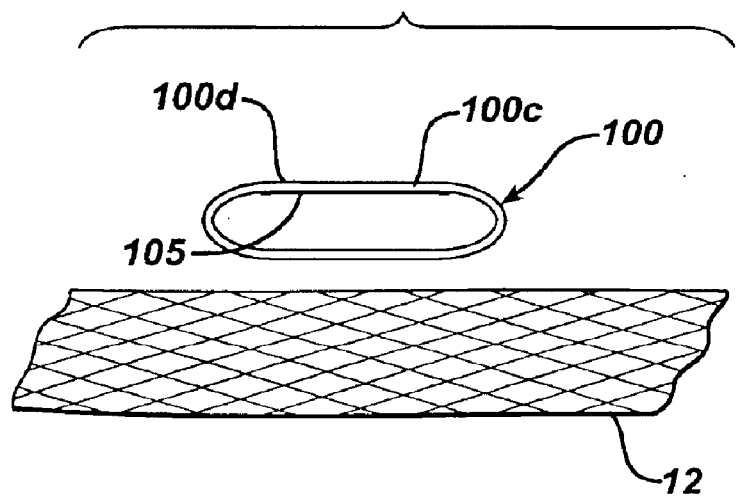
Figure 4F:
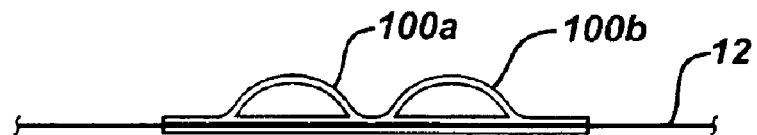

FIG. 4e discloses a double walled self-sealing container 100 that eliminates the need for a separate injection port. Container 100 comprises an inner chamber 100c that preferably contains a centrally located plastic or metal barrier 105 to prevent needle penetration through the far wall while injecting the bulking agent. While injecting the bulking agent using, for example, a needle, puncture holes are created in the walls of the inner and outer chamber 100c, 100d, respectively. After removal of the injecting device, exact alignment of the inner and out chamber puncture holes is shifted. This shift results in effectively sealing the injection site.

Alternatively, a single walled self-sealing container may be used. The inner layer of such a container may have a soft plastically deformable coating. The coating acts to fill-in any injection puncture site resulting in sealing the container.

Figure 5A:
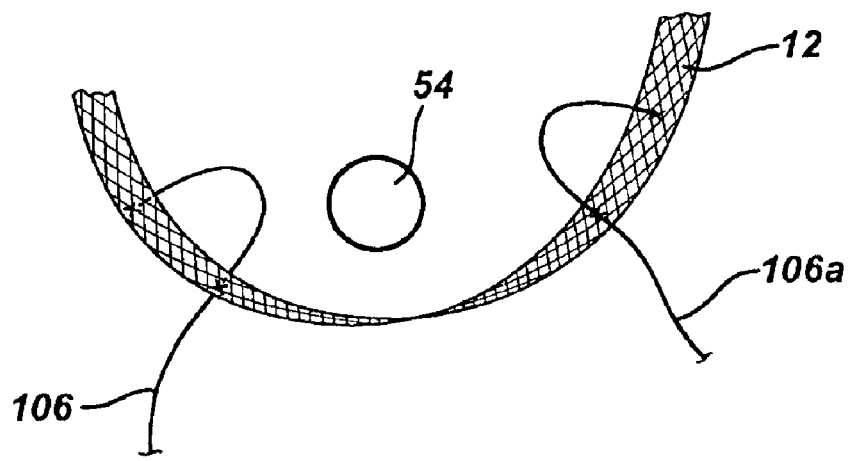
FIGS. 5a–c are alternate embodiments for providing mechanical adjusting means to the tape mesh.
Figure 5B:
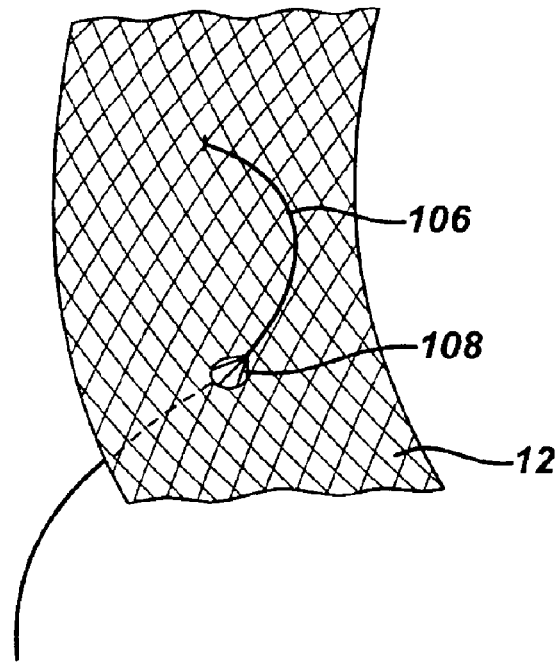
Figure 5C:
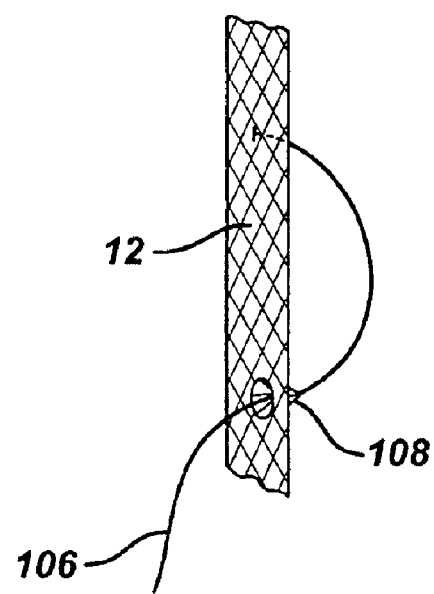

Tape 12 may be further modified to include a mechanical adjustment means to adjust the tape 12 after it has been implanted as discussed below. The mechanical adjustment means incorporate a suture 106 and 106a preferably located on either side of the central portion of the tape 12 as shown in FIGS. 5a–c.

Sutures 106 and 106a can be used in combination with a one-way suturing retaining device 108 as is disclosed in U.S. Pat. No. 5,669,935, which is incorporated in its entirety by reference herein. Retaining device is anchored to tape 12 using any biocompatible adhesive or attachment as is known to those skilled in the art. Another means includes a tie-wrap-type mechanism to adjust the length of one or both sides of the tape 12 in near proximity to the urethra 54 and similarly positioned as sutures 106, 106a. In either instance, the sutures 106, 106a or tie wrap remain accessible through the incision in the vagina, discussed below, for a period of time after tape implantation. Tape adjustment would be suitable for a number of days following the procedure before serious tissue ingrowth occurs. Afterward, the exposed sutures or tie-wrap may be cut.

In one embodiment tape 12 may be attached to needle segment 20 by means of tying, gluing or other suitable attaching means. Preferably, a biocompatible heat shrink tube fixes tape 12 onto needle portion 20, FIG. 2a. In a further embodiment, as shown in FIGS. 2b–d and 3a–h, needle 10 and tape 12 are further configured to enable easy attachment and detachment of tape 12 to and from needle 10 by the surgeon during the operation. This embodiment allows for the use of a single needle for the procedure. This embodiment also allows for the use of a tape constructed, at least in part, of natural materials, which are otherwise not suitable in the pre-affixed embodiment due to the inability of the natural material to survive extended periods in inventory.

Figure 2D:
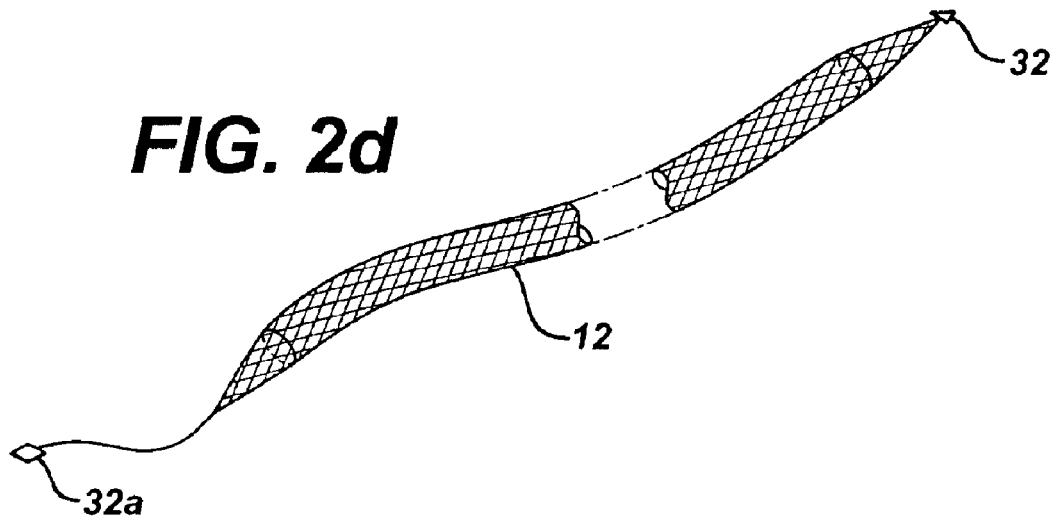
Figure 3A:
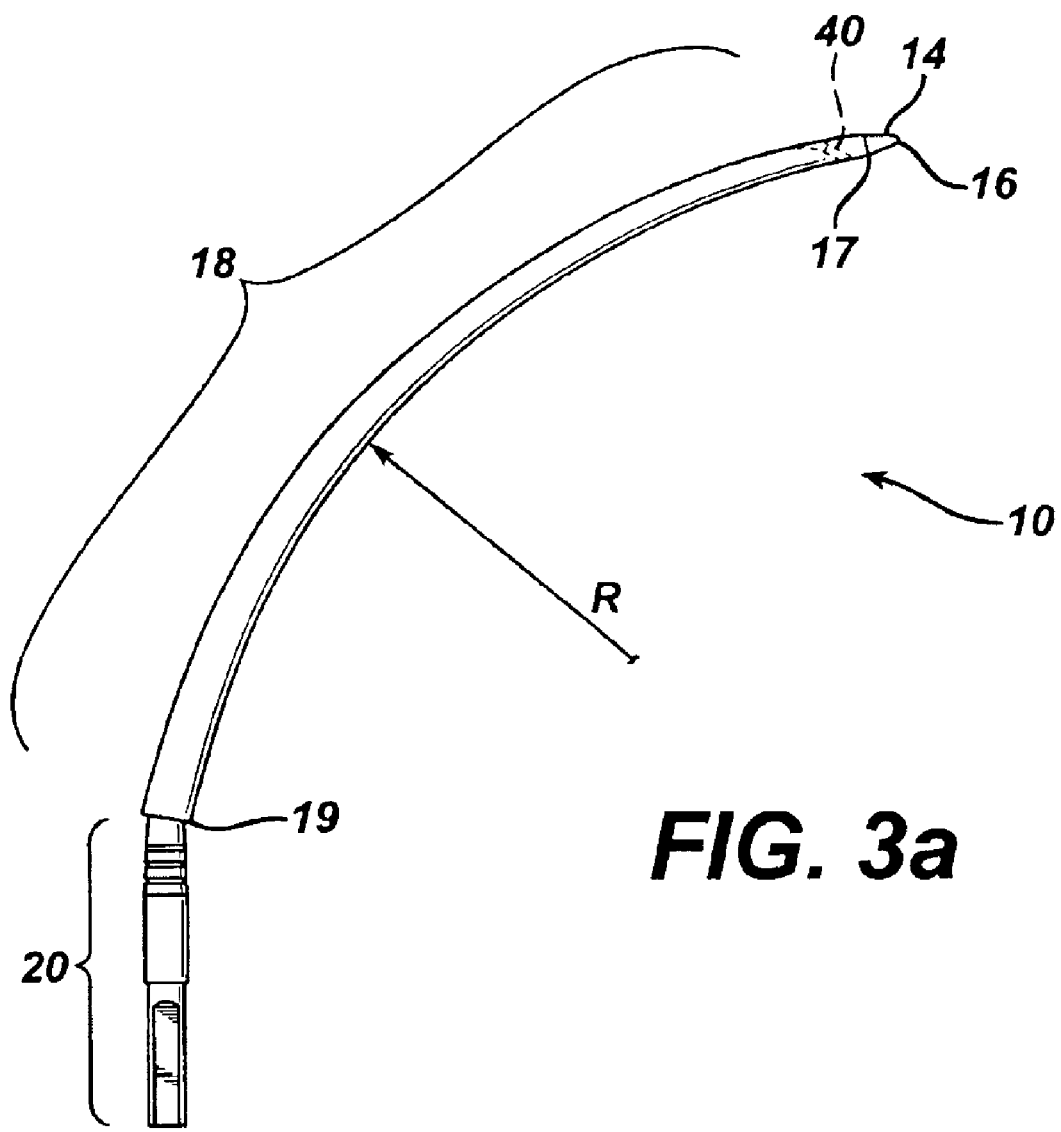

In one embodiment, shown in FIGS. 3a–c, shaft 18 provides for a notch or slot 40 to slidably receive connecting tabs 32 and 32a that are attached at either ends of tape 12 (FIGS. 2b–d). Preferably, slot 40 extends through curved shaft 18 and is further located at the distal end 17 of needle 10 so that tape 12 may be disconnected from needle 10 immediately after needle 10 penetrates the abdomen wall, discussed below.

Tab 32 may be constructed from any bio-compatible material, such as plastic or metal. Tab 32 can be any shape, such as a square or arrow shape, so long as tap 32 can be securely inserted into notch or slot 40. FIG. 3b–c illustrates tab 32 having two spring arms 33 and 33a that when inserted into slot 40 expand and securely fasten tab 32 within slot 40. Tab 32 may be attached to tape 12 in any number of convenient methods as previously discussed and well known to those skilled in the art.

FIG. 3d–e illustrates a two-tier slot 40, wherein tab 32 and spring element 33b slide into the lower tier which holds tab 32 in place. Alternate means of capturing tab 32 within slot 40 are available as is well known in the art.

FIGS. 3f–g illustrate an alternate embodiment of affixing tape 12 to the distal end 17a of needle 10. A detachable blunt tip 16a having a connecting post 15, attaches to the distal end 17a by means of a mounting hole 15a to accept post 15. Post 15 may be securely attached to hole 15a either by compression fit, mating threads or other convenient attachment methods. Distal end 17a further defines a groove 23 of varying depth to allow the end of tape 12 connected to post 15 to transition from within hole 15a to the exterior of needle 10. Along with the embodiment of FIGS. 3a–e, this embodiment allows the surgeon to affix tape 12 to needle 10 just prior to the surgical procedure. One advantage is the ability to use a tape 12 constructed of, at least in part, a natural material 13.

As would be appreciate by one skilled in the art, there exist multiple means for detachably connecting the tape to the needle. Alternate embodiments would include tying the ends of tape 12 to form a knot and securely inserting the knot into a V-type groove in shaft 18. Alternately, a diagonal slit in shaft 18 could accept tape 12 or a suture extending from tape 12.

The surgical procedure for implanting tape 12 using two needles is shown in FIGS. 6a–h utilizing the needle embodiment illustrated in FIGS. 1 and 2a. In the figures the relevant parts of the female lower abdomen are disclosed, the vagina being 50, the uterus 52, the urethra 54, the pubic bone 56, the urinary bladder 58 s and the abdominal wall 60. The first needle 10a penetrates the vaginal wall, an incision having first been made in the wall to create a tissue flap. The needle is attached to handle 411, and, the surgeon guides needle 10a through the vaginal wall and through the soft tissue on one side of the urethra 54, the needle then according to FIG. 6b being passed close to the back of the pubic bone 56, through additional layers of fat, muscle and fascia, and then through the abdominal wall 60 above the pubic bone 56. An incision can be made through the abdominal wall for the passage of the needle there through. The handle 411 is disconnected from needle 10a, FIG. 6c, and the needle 10a along with tape 12 are withdrawn from the abdomen wall by means of forceps, FIG. 6d.

Figure 6A:
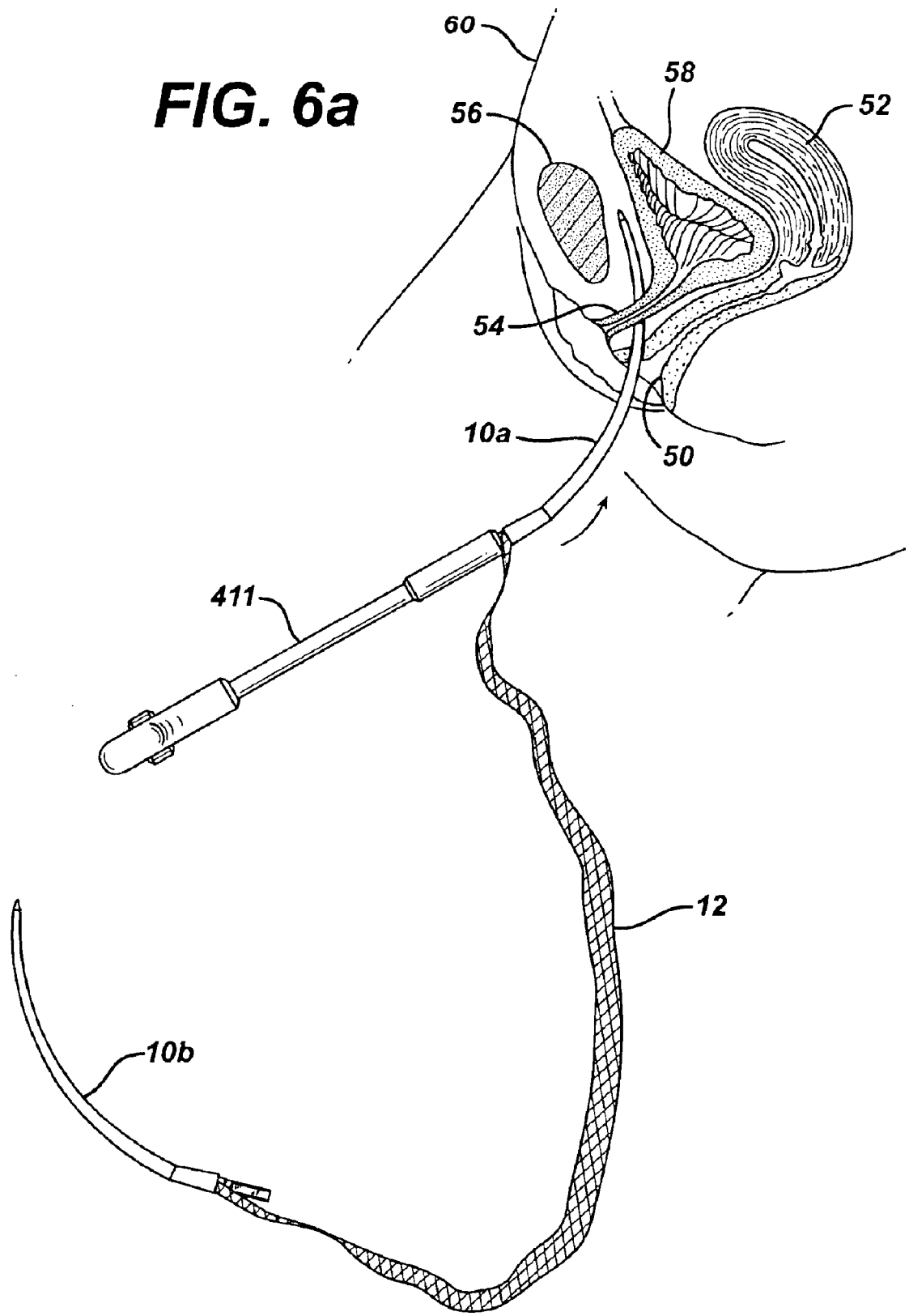
FIGS. 6a–h illustrate diagrammatically several surgical steps of the method utilizing two needles according to the invention to treat SUI.
Figure 6B:
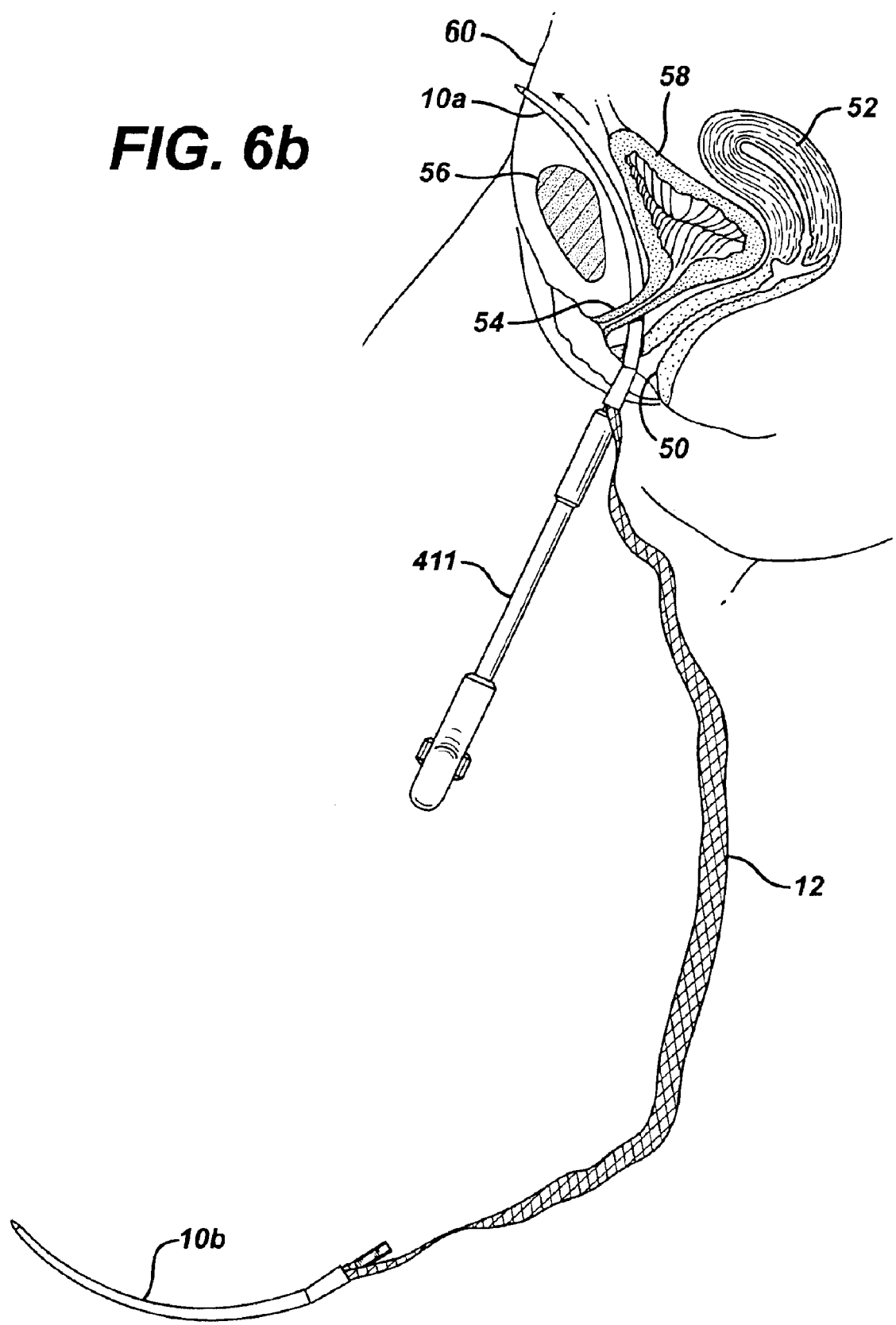
Figure 6C:
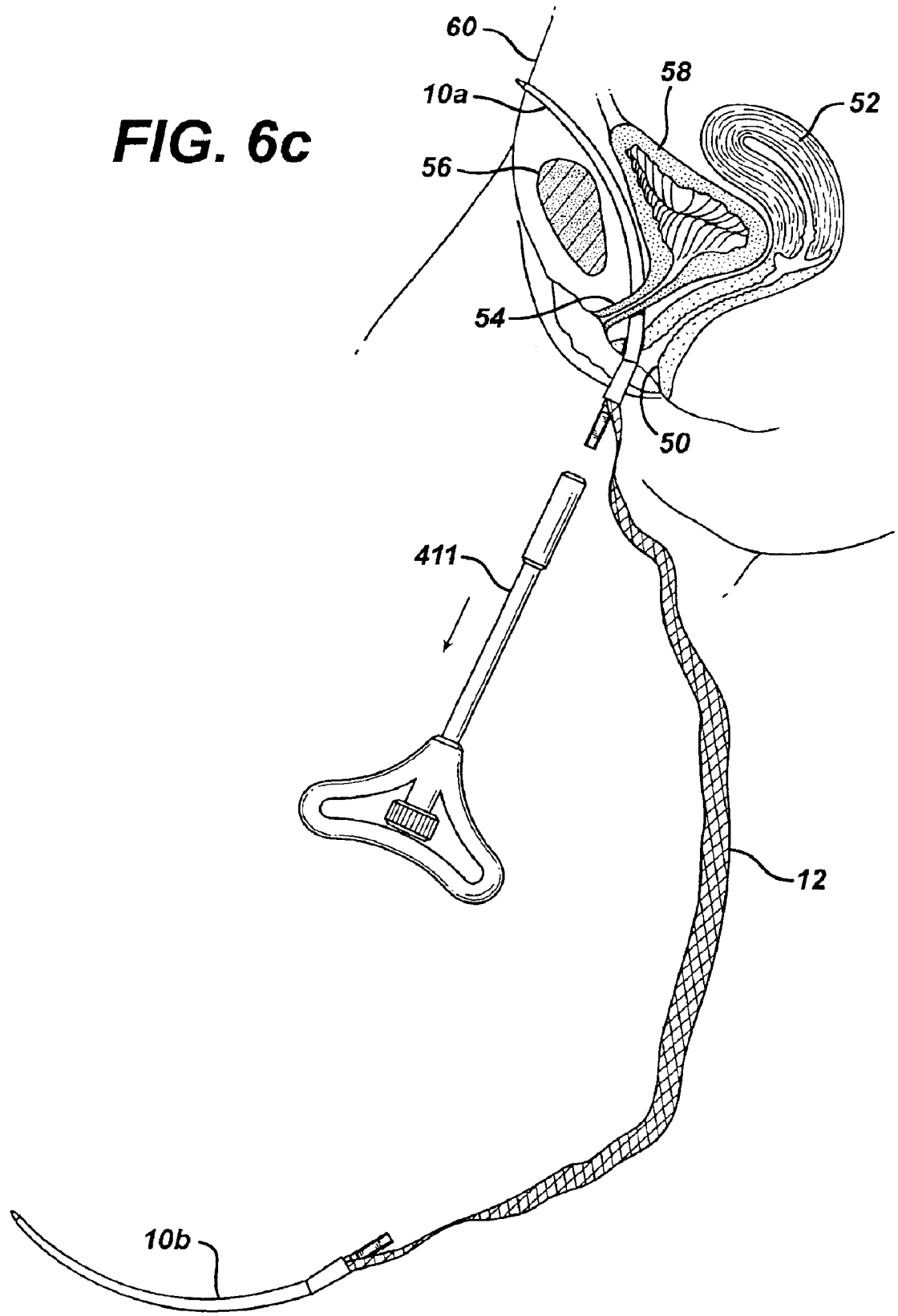
Figure 6D:
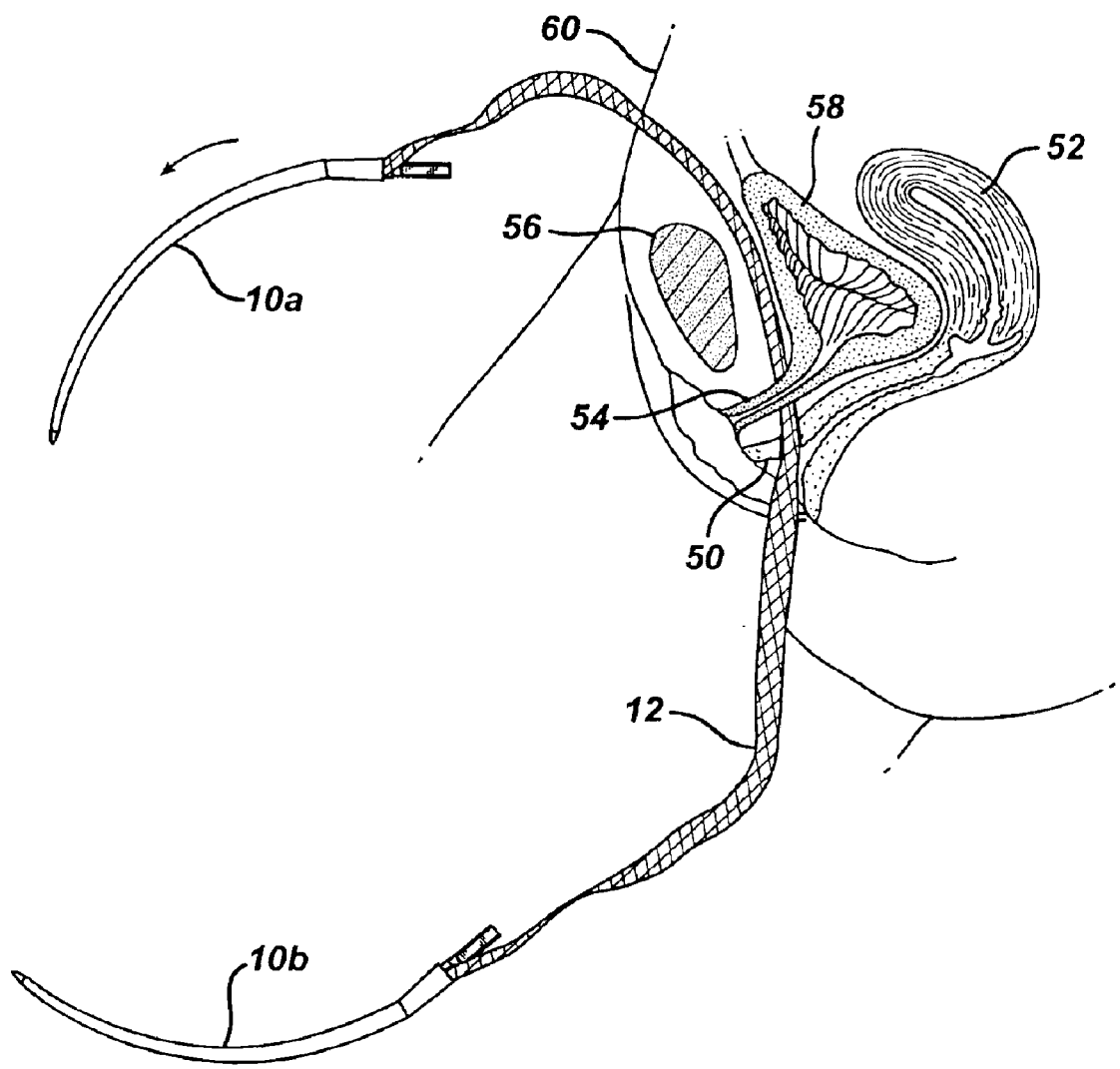
Figure 6E:
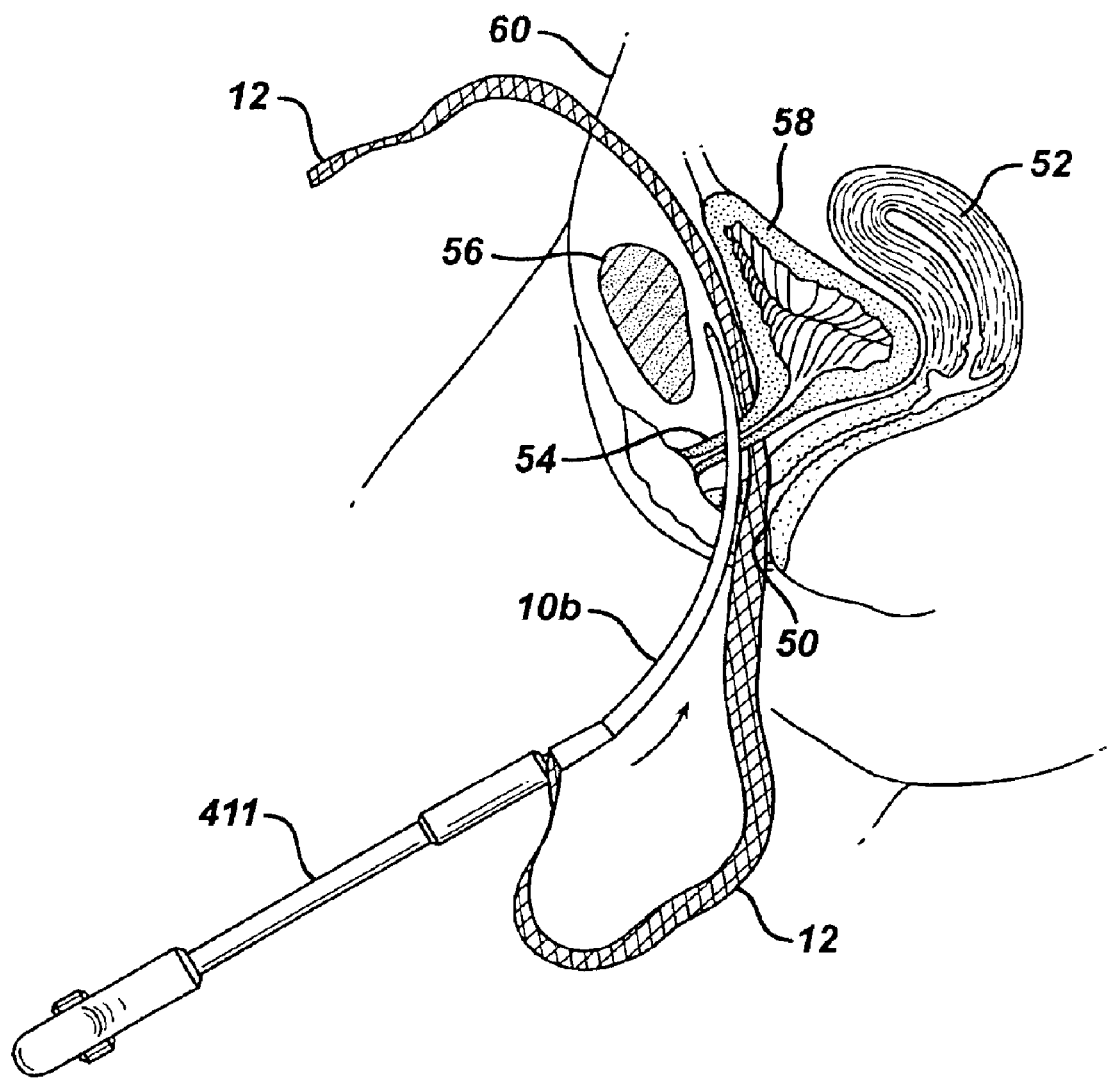
Figure 6F:
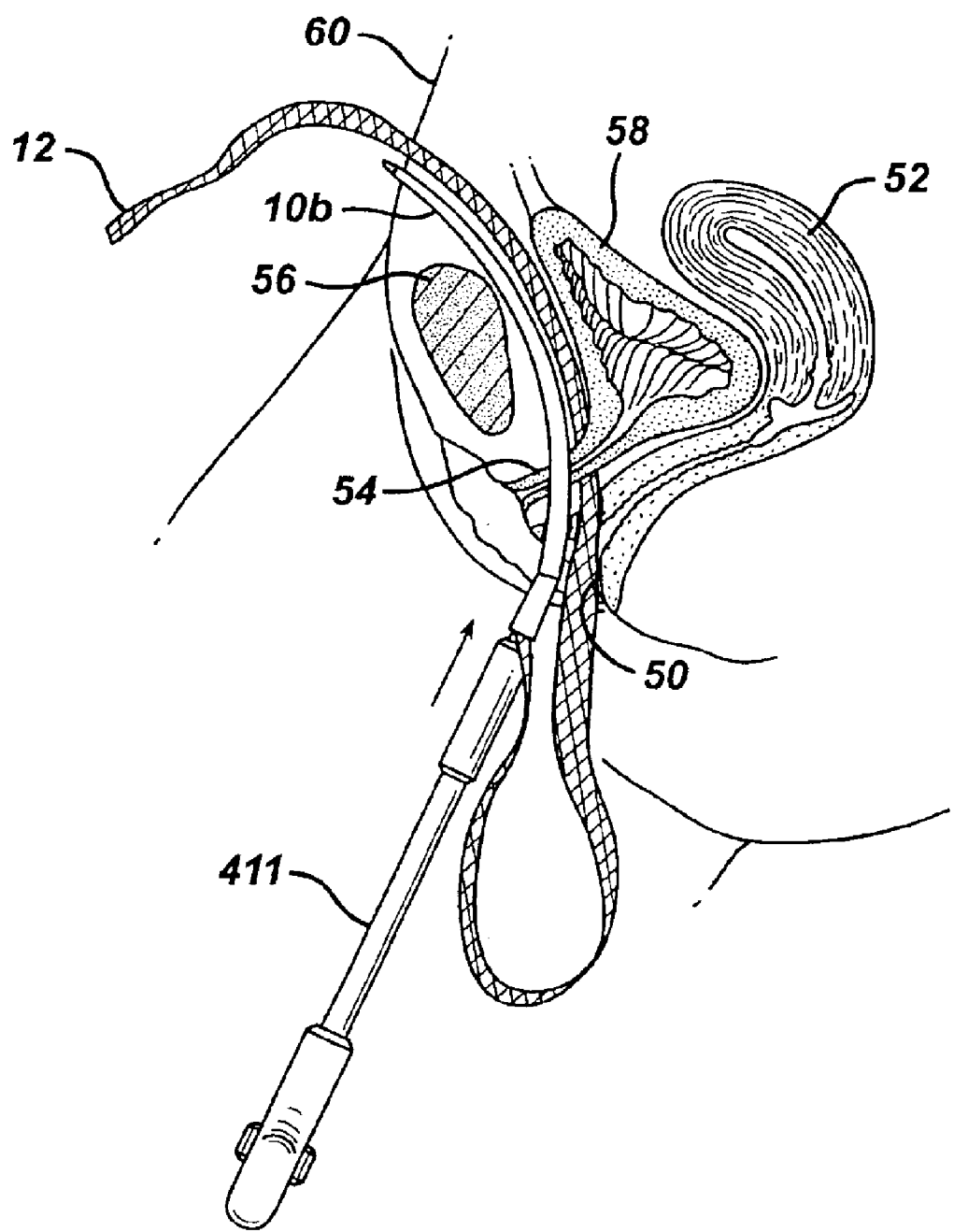
Figure 6G:
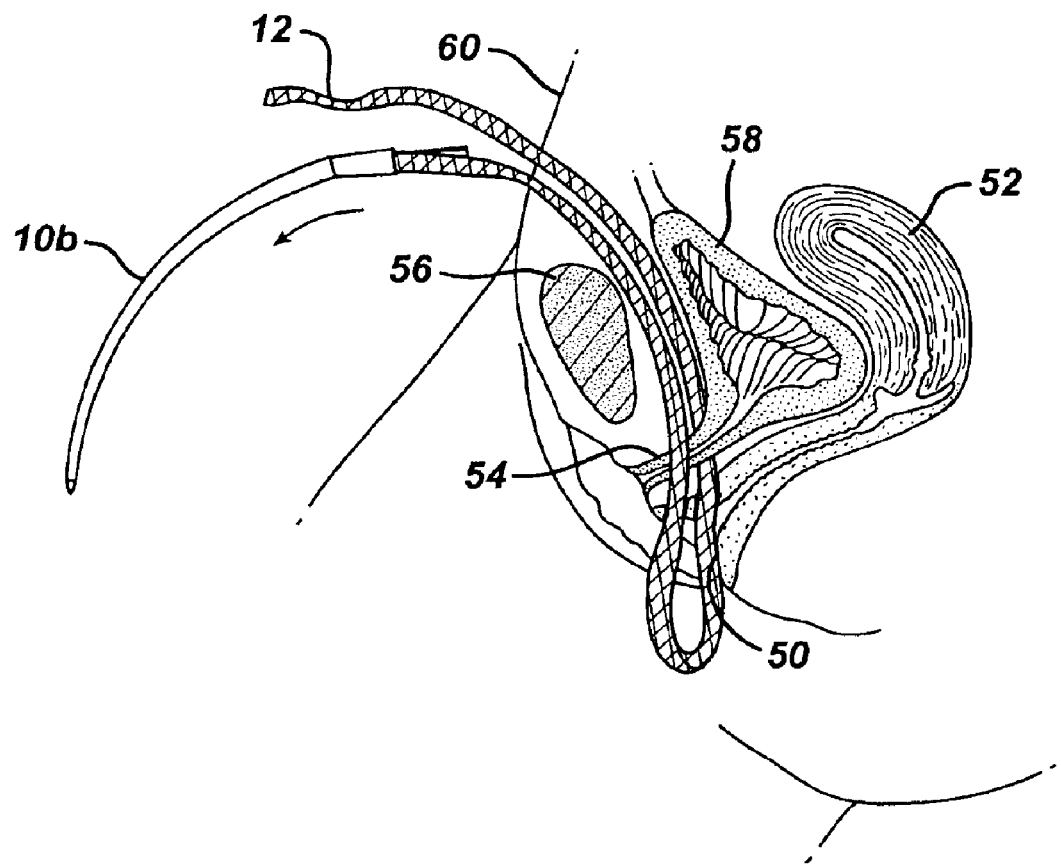
Figure 6H:
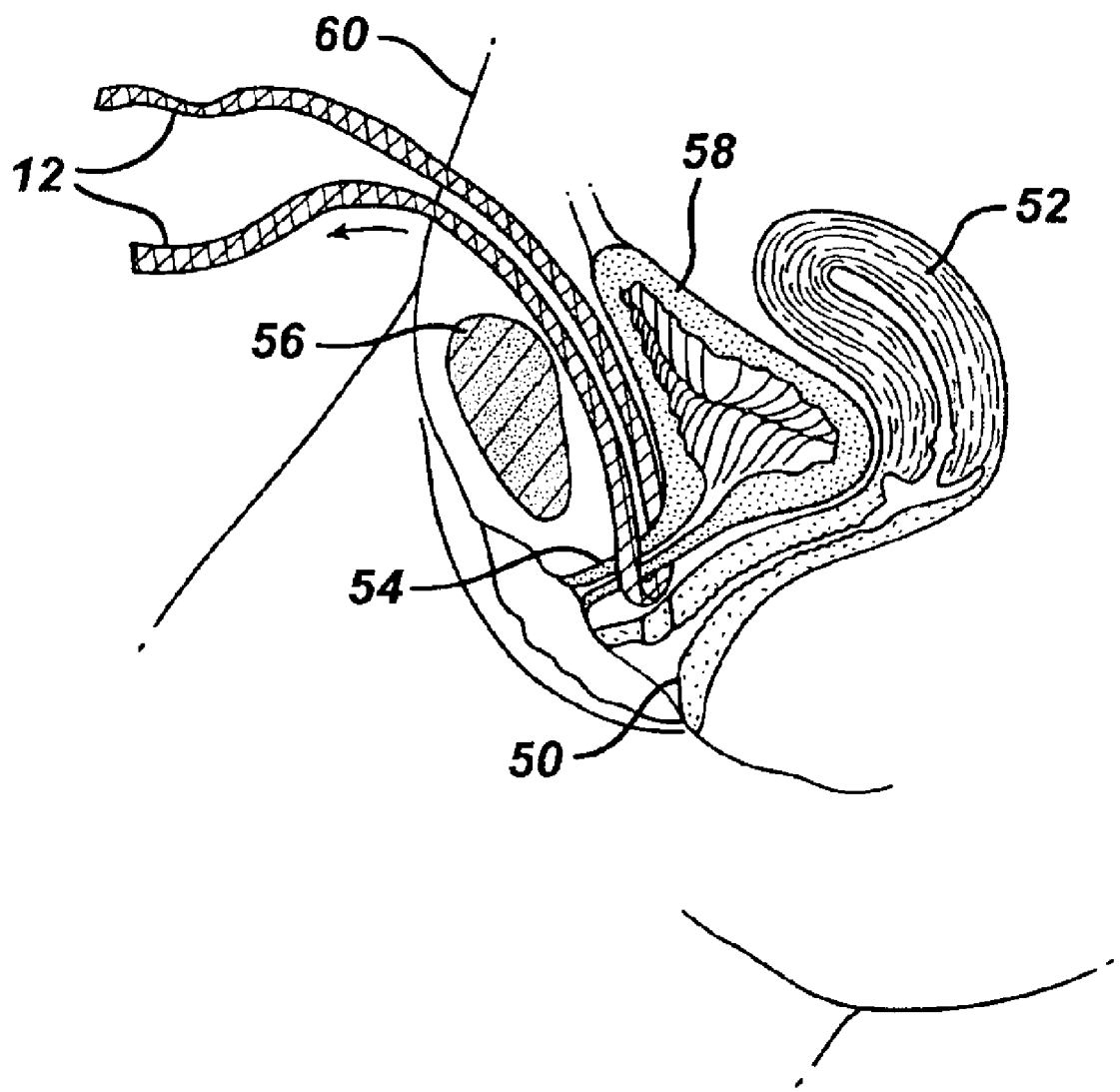

Referring to FIG. 6e, needle 10b is now attached to handle 411. The surgeon passes needle 10b through the incision in the vaginal wall and through the soft tissue, again, on the opposite side of the urethra than the previous end of tape 12. Needle 10b passes close to the back of the pubic bone, through additional layers of fat, muscle and fascia, FIG. 6f, and then through the abdominal wall above the pubic bone and withdrawn, FIG. 6g.

FIGS. 7a–g illustrate an alternate method of implanting tape 12 using a single needle 10. Tape 12 is attached to needle 10 by means of spring tab 32 as shown in FIGS. 3b–c. Needle 10 penetrates the vaginal wall, an incision having first been made in the wall to create a tissue flap. The surgeon guides needle 10 through the vaginal wall and through the soft tissue on one side of the urethra 54, the needle then according to FIG. 7b being passed close to the back of the pubic bone 56, through additional layers of fat, muscle and fascia, and then through the abdominal wall 60 above the pubic bone 56. An incision can be made through the abdominal wall for the passage of the distal end 17 there through. Needle 10 only continues to pass through the abdominal wall until tap 32 may be disconnected from needle 10, FIG. 7c. To do so, the surgeon simply pushes tab 32 through slot 40 using an appropriate instrument and cuts tab 32 pulls out tab 32 using forceps. Tab 32 may then be cut off and tape 12 may be pulled out of the abdominal wall to allow the surgeon additional length for the procedure. Needle 10 is then removed from the patient along the same path that it entered, but in the opposite direction, FIG. 7d. Alternatively, needle 10 may be disconnected from handle 411 and pulled out through the abdomen wall 60 using forceps as discussed with regard to the two needle procedure.

Needle 10 is now attached to the opposite end of tape 12 using connector tab 32a. The surgeon passes needle 10 through the incision in the vaginal wall and through the soft tissue on the opposite side of the urethra than the previous end of tape 12, FIG. 7e. Needle 10 passes close to the back of the pubic bone, through additional layers of fat, muscle and fascia, FIG. 7f, and then through the abdominal wall above the pubic bone. Needle 10 continues to pass through the abdominal wall only until tab 32a may be disconnected from needle 10, FIG. 7g. Tape 12 may be pulled out of the abdominal wall to allow the surgeon additional length for the procedure. Needle 10 is then removed from the patient along the same path that it entered, but in the opposite direction. Alternatively, needle 10 may be disconnected from handle 411 and pulled out through the abdomen wall 60 using forceps.

Figure 7A:
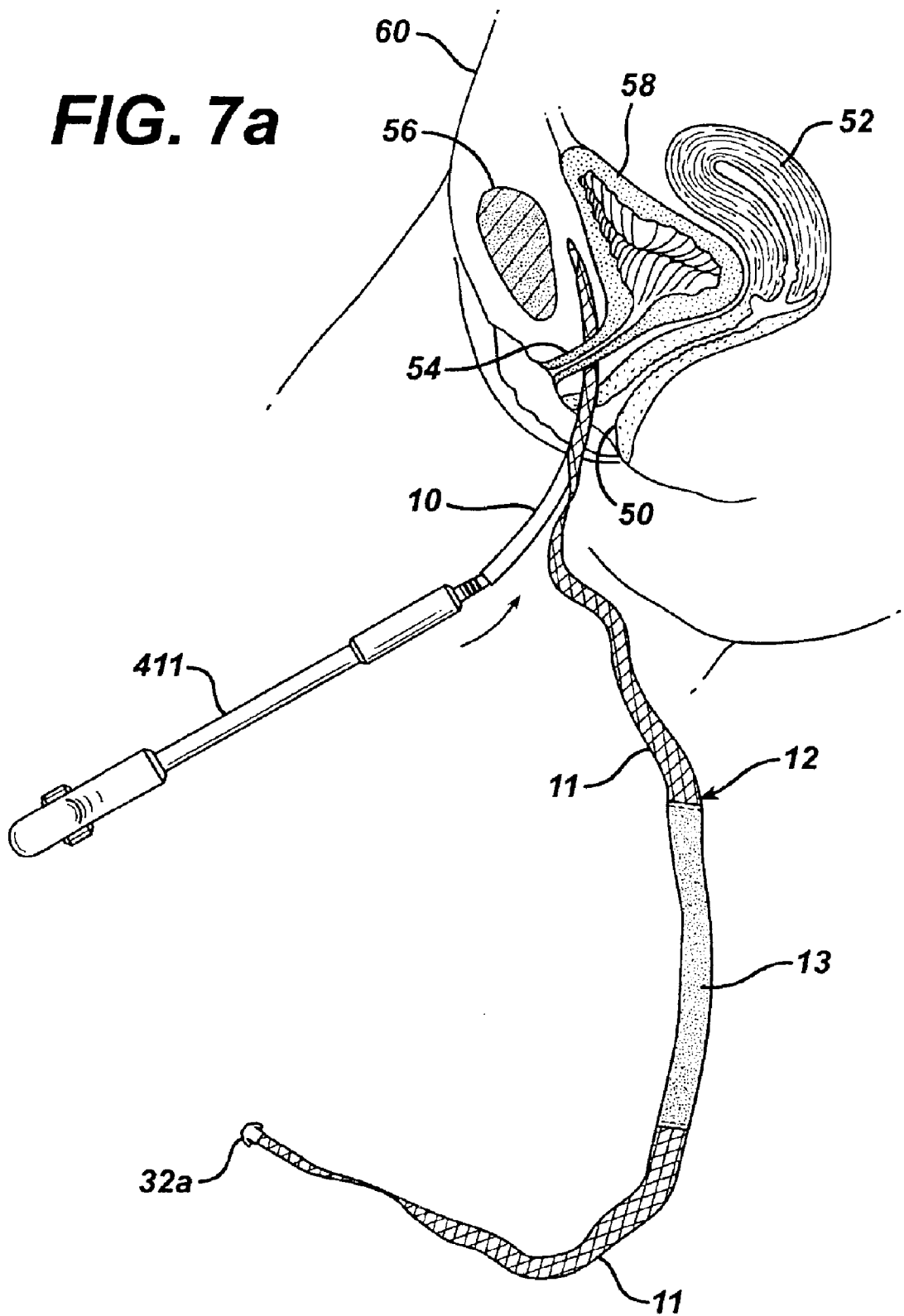
FIGS. 7a–h illustrate diagrammatically surgical steps of the method utilizing one needle according to the invention to treat SUI.
Figure 7B:
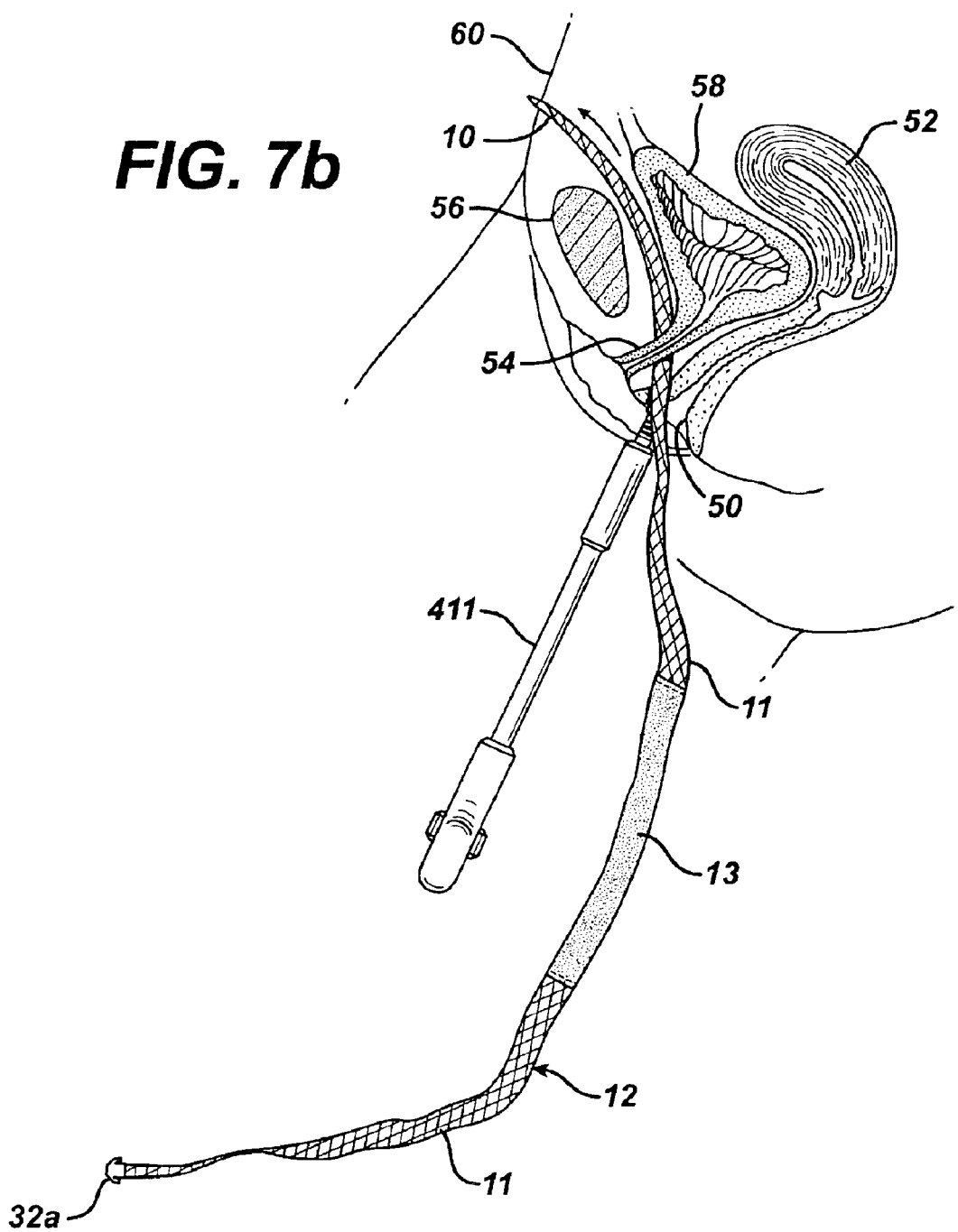
Figure 7C:
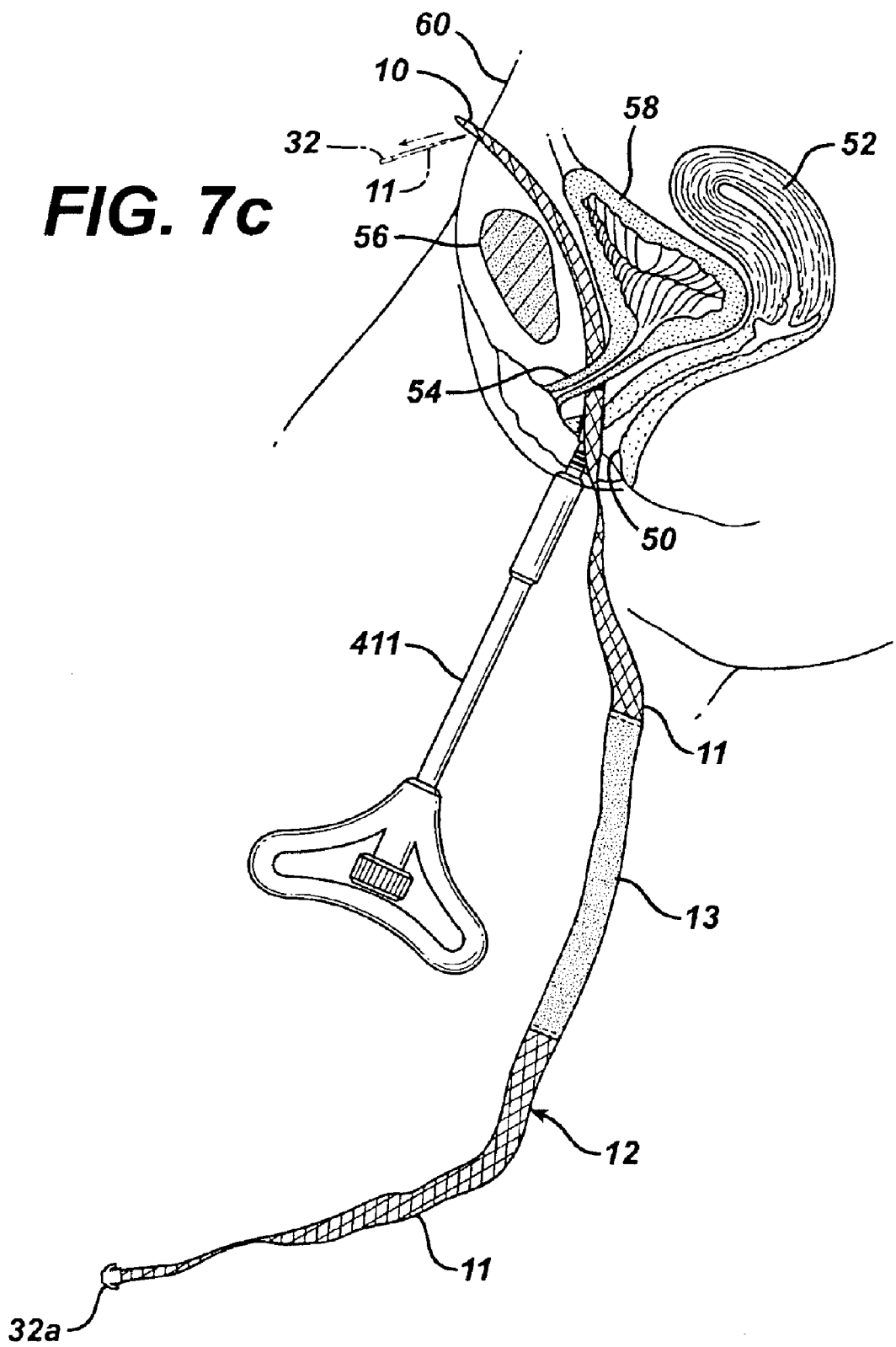
Figure 7D:
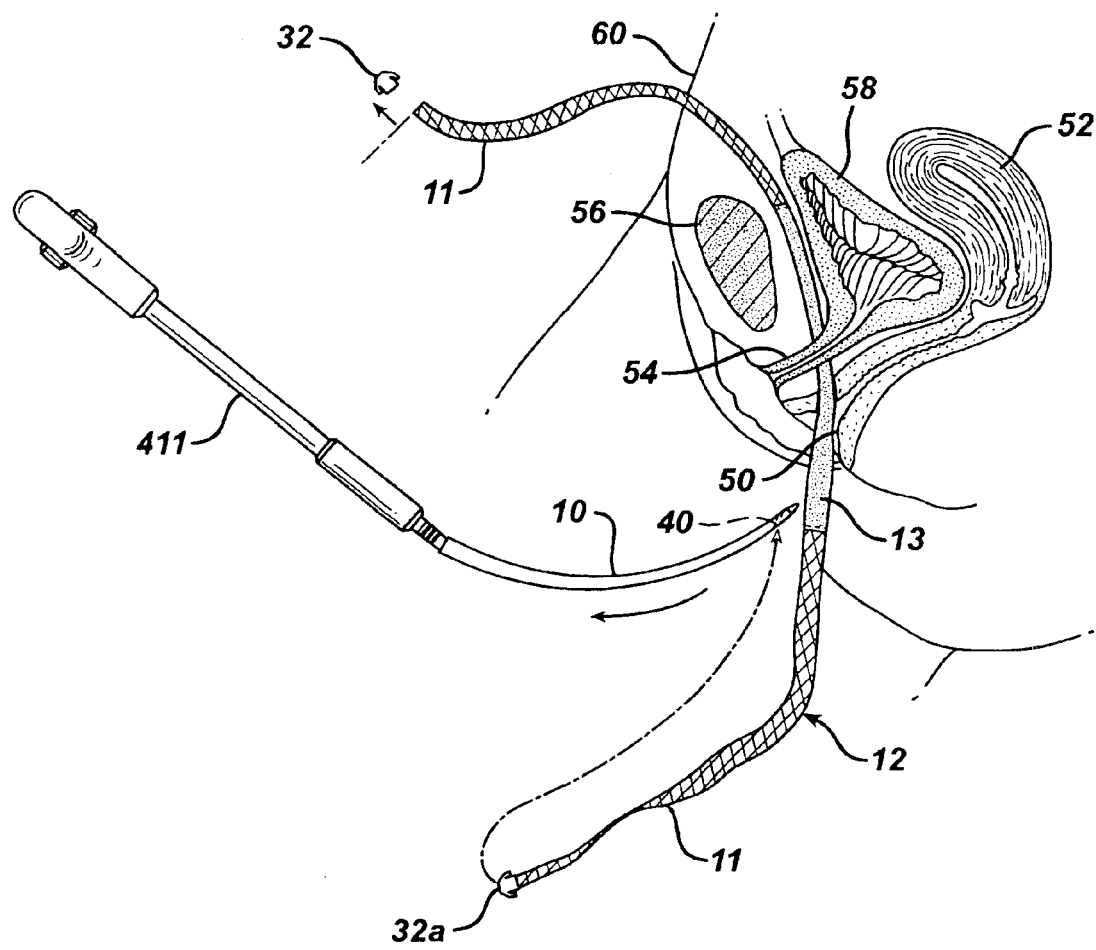
Figure 7E:
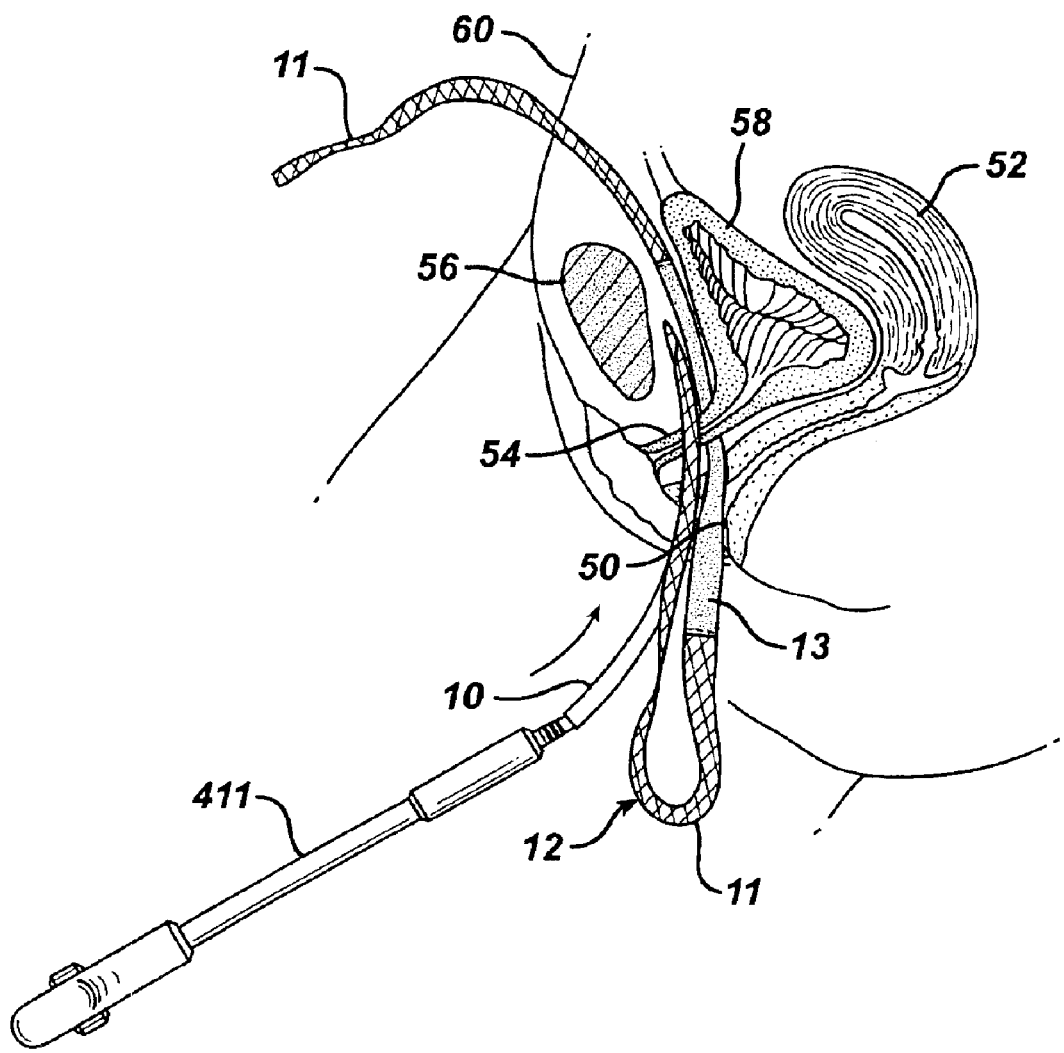
Figure 7F:
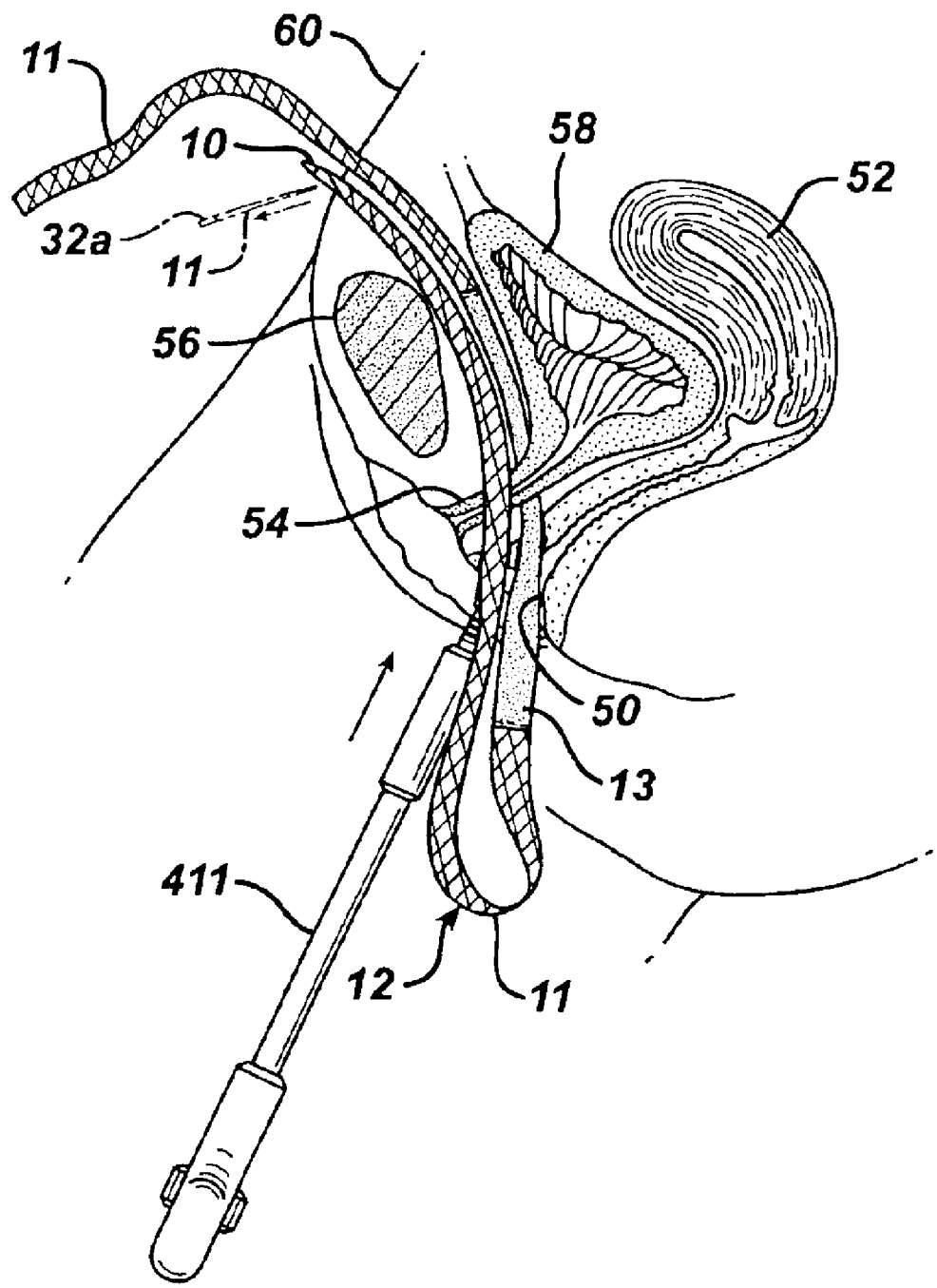
Figure 7G:
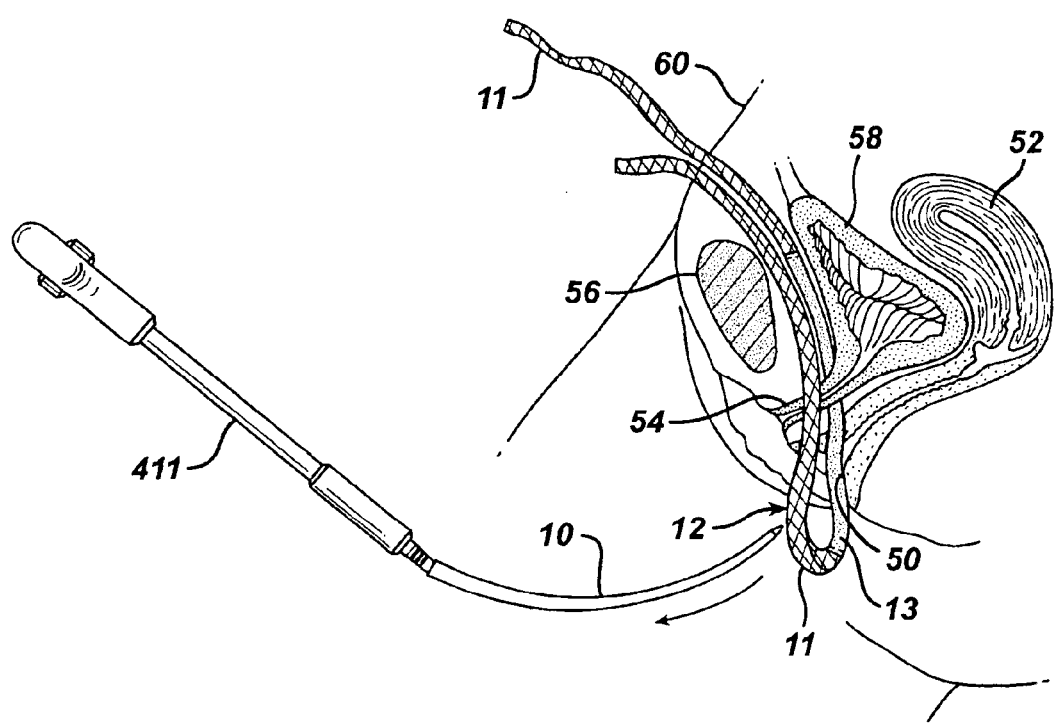
Figure 7H:
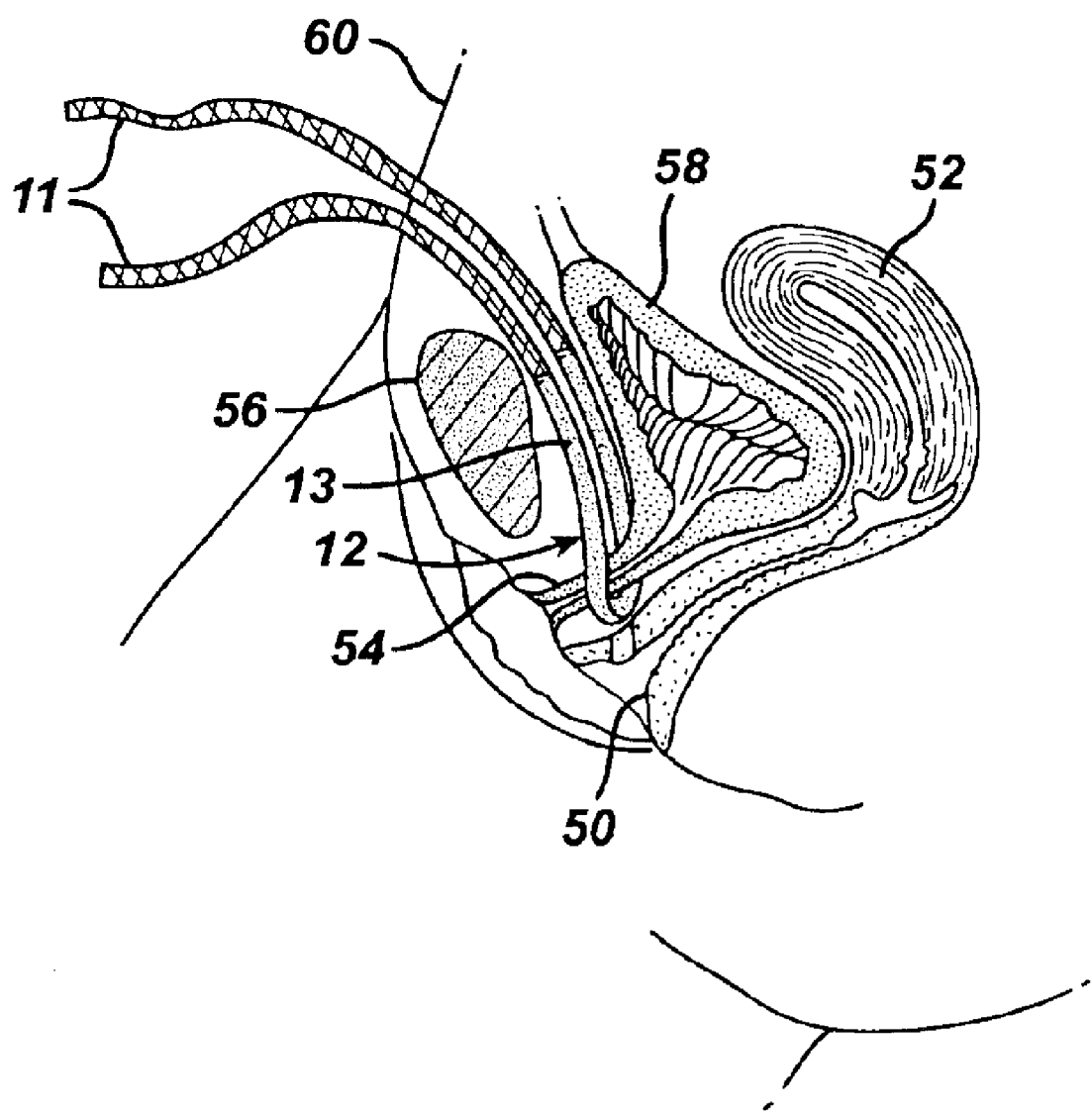

Since both procedures may be performed using a local anesthesia, the patient is able to provide feedback to the surgeon after tape 12 is in place. Typically, the urinary bladder 58 is filled with a fluid, such as water, using a catheter and the patient is requested to cough. The surgeon is able to determine the operation of the urethra and may adjust the tape 12, as necessary, by adjusting the ends of tape 12 located at the outside of the abdomen 60, FIGS. 6h and 7h. After adjustments, the surplus tape at the abdomen is cut off, and the ends of the tape are secured within the abdomen and the abdomen is closed. Likewise, the incision at the vaginal wall is closed whereby the tissue flap seals the tape between the urethra 54 and the wall of vagina 50.

Tape 12 is left in the body and forms an artificial ligament attached to the abdominal wall that provides the support for the urethra as required in order to restore urinary continence to the patient.

At the end of either procedure disclosed in FIGS. 6 and 7, the surgeon may perform a test procedure to determine the integrity of the urinary bladder. A hydraulic diagnosis of the bladder may be performed by placing a rigid endoscope/sheath transurethrally and injecting fluid through the sheath into the bladder. The bladder is pressurized to a known level, about 50 mm Hg as measured through the sheath. If the pressure is maintained, then the surgeon can be confident that the bladder has not been perforated. Conversely, if the bladder loses pressure, steps can be taken to repair any defects.

Figure 8:
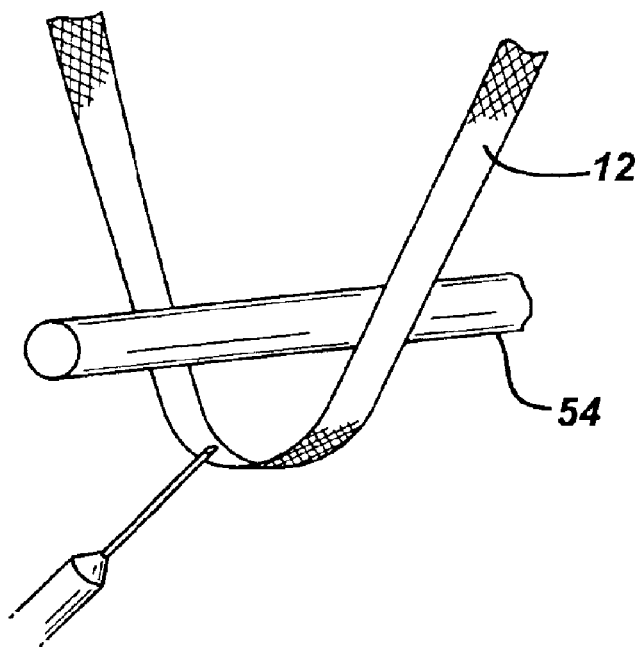
FIG. 8 is diagrammatic representation illustrating direct bulking between the tape and urethra.

Post-surgical adjustment of the tape may be accomplished by injecting bulking agents in the vicinity of the tape sling so as to effect additional support to the urethra. Preferably the bulking agent would be injected at the top of the mesh so as to expand the tissue between mesh and urethra (direct bulking) as shown in FIG. 8. This procedure may be used in combination with a tape 12 having a expandable chamber or used alone. Suitable direct bulking agents include DURASPHERES, CONTIGEN, MACROPLASTIQUE as well as polytetrafluorethylene, and synthetic, natural slowly absorbable or nonabsorbable materials. Bulking agents must be stable, biocompatible and, in the case of direct injection without a container, should be resistant to migration. The bulking agent may be detectable (eg., radiopaque) such as the case with DURASPHERES or may contain a contrast component that allows for visualization of the amount and location of the agent To inject a bulking agent into container 100 (FIGS. 4a–f), the surgeon would palpate the area to detect the injection site for the container, and if needed, a small incision in the vaginal wall may be made. Alternatively, markers may be either separate or an integral part of the container or tape. For example, ultrasound may be used to provide guided injection. This may be achieved preferably by rectal placement of the transducer. A suitable bulking agent may then be injected using only local anesthesia, transvaginally or transurethrally.

Figure 9:
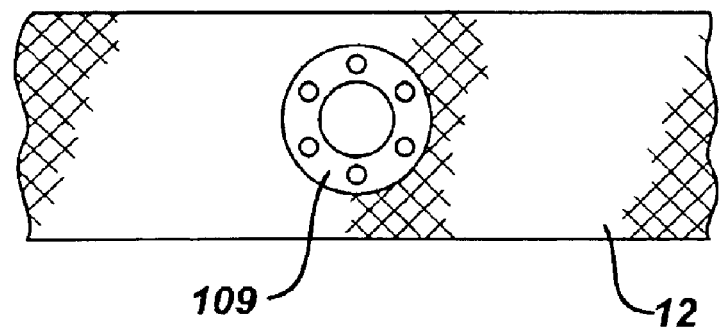
FIG. 9 is a representation of a detectable target ring implanted in the tape.

The ultrasonic diagnostic detectability of the targeting region could be improved by radiopaque beads if desired. Referring to FIG. 9, an x-ray detectable polypropylene (for example, Prolene, provided by Ethicon, Inc.) foil ring 109 may be used. An exemplary ring 109 has an inner diameter of 0.5 cm and an outer diameter of 1 cm and a thickness of 0.5 mm and contains six 1.5 mm diameter zirconiumdioxide beads (95% $ZrO_2$ /5% $Y_2O_3$ provided by Muhimeyer Mahlechnik, Germany) as radiopacifiers around an opening in the mesh 12. Ring 109 is affixed to the center of tape 12 using ultrasonic welding. These x-ray radiopacifiers are suitable implant materials and are also visible in ultrasound.

Ring 109 may also be used for x-ray-guided injection. After tape implantation, the area around the tape may be expanded with a bulking agent using guidance provided by x-ray visualization. Exact positions of the target ring 109 and (and corresponding tape), radiopacified-filled urethra, bladder and bulking agent (for example, radiopaque DURASPHERES) may be determined through the use of computerized tomography.

It will be apparent from the foregoing that, while particular forms of the invention have been illustrated and described, various modifications can be made without departing from the spirit and scope of the invention. Accordingly, it is not intended that the invention be limited, except as by the appended claims.

We claim:

1. A surgical instrument for treating female urinary stress incontinence comprising:

a) a substantially flat, flexible tape for implanting into the lower abdomen of a female patient to provide support to the urethra, and having a length and a width; and b) a filamentary element that is distinct from and does not form part of the tape, the filamentary element extending along at least a portion of the length of the tape and having a first end permanently affixed at a first position to the tape and a second end, the filamentary element passing through the tape at least once, at a second position different from the first position whereby manipulation of the filamentary element increases or decreases tension on the tape, thereby providing increased or decreased support to the urethra respectively.

2. The surgical instrument according to claim 1, wherein the filamentary element is a suture.

3. The surgical instrument according to claim 1, wherein the filamentary element is positioned substantially along a center of the tape.

4. The surgical instrument according to claim 1, wherein the filamentary element is woven through the tape at a plurality of locations.

5. A method for treating female urinary incontinence comprising the steps of:
  a) providing a substantially flat tape for implanting into the lower abdomen of a female patient to provide support to the urethra, the tape having a width and a length,
  b) providing an expandable chamber for accepting a fluid therein affixed to the tape, the filamentary element extending along at least a portion of the length of the tape, and having a first end permanently affixed at a first position to the tape and a second end and passing through the tape at least once at a second position at a second position different from the first position, and
  b) manipulating the filamentary element to increases or decreases tension on the tape to thereby increase or decrease respectively support to the urethra.

6. The method according to claim 5, wherein the filamentary element is a suture.

7. The method according to claim 5, wherein the filamentary element is positioned substantially along a center of the tape.

8. The method according to claim 5, wherein the second end of the filamentary element is accessible via the patients vagina.

9. The method according to claim 5, wherein the filamentary element is woven into the tape at a plurality of locations.

10. A surgical instrument ortreating female urinary stress incontinence comprising:
  a) a substantially flat flexible tape for implanting into the lower abdomen of a female patient to provide support to the urethra, and having a length and a width; and
  b) a filamentary adjustment element that is distinct from and does not form part of the tape, the filamentary adjustment element extending along at least a portion of the length of the tape and substantially centered relative to the width of the tape, the filamentary adjustment element being permanently affixed to the tape at at least one location, and passing through the tape at least once at after location different from the at least one location, whereby manipulation of the filamentary element adjusts the tape to thereby increase or decrease support to the urethra.

11. The surgical instrument according to claim 10, wherein the filamentary adjustment element is a suture.

12. The surgical instrument according to claim 10, wherein the filamentary adjustment element extends substantially along the length of the tape that is implanted within the patient.

13. The surgical instrument according to claim 10, wherein the filamentary adjustment element is positioned to one side of the urethra.

14. The surgical instrument according to claim 13, further comprising a second filamentary adjustment element that is distinct from and does not form part of the tape, the second filamentary adjustment element extending along a second portion of the length of the tape that is positioned on the other side of the urethra being substantially centered relative to the width of the tape, and being affixed to the tape at least one location and passing though the tape at least once.

* * * * *

UNITED STATES PATENT AND TRADEMARK OFFICE
CERTIFICATE OF CORRECTION

| | | |
|---|---|---|
| PATENT NO. | : 7,083,637 B1 | Page 1 of 1 |
| APPLICATION NO. | : 09/589242 | |
| DATED | : August 1, 2006 | |
| INVENTOR(S) | : Robert J. Tannhauser | |

It is certified that error appears in the above-identified patent and that said Letters Patent is hereby corrected as shown below:

col. 12, cl. 10, ln. 1 change "ortreating" to --for treating--;
                 ln. 13 delete "after" and insert --another--:
col. 12, cl. 14, ln. 7 after "at" insert --at--.

Signed and Sealed this

Fifteenth Day of May, 2007

JON W. DUDAS
*Director of the United States Patent and Trademark Office*